United States Patent [19]

Gaudet et al.

[11] Patent Number: 6,052,654
[45] Date of Patent: *Apr. 18, 2000

[54] MEASURING FOOT CONTACT TIME AND FOOT LOFT TIME OF A PERSON IN LOCOMOTION

[75] Inventors: Paul J. Gaudet, Tewksbury; Thomas P. Blackadar, Natick; Steven R. Oliver, Attleboro, all of Mass.

[73] Assignee: Personal Electronic Devices, Inc., Wellesley Hills, Mass.

[*] Notice: This patent is subject to a terminal disclaimer.

[21] Appl. No.: 09/364,559

[22] Filed: Jul. 30, 1999

Related U.S. Application Data

[63] Continuation of application No. 08/942,802, Oct. 2, 1997.
[51] Int. Cl.[7] ................................................. G04F 10/00
[52] U.S. Cl. ........................ 702/160; 702/144; 702/176; 73/597; 324/160
[58] Field of Search ................................. 702/160, 176, 702/144; 73/597; 324/160

[56] References Cited

U.S. PATENT DOCUMENTS

| 4,409,992 | 10/1983 | Sidorenko et al. | 128/782 |
| 4,757,714 | 7/1988 | Purdy et al. | 73/597 |
| 5,636,146 | 6/1997 | Flentov et al. | 702/176 |
| 5,955,667 | 9/1999 | Fyfe | 73/490 |

*Primary Examiner*—Marc S. Hoff
*Assistant Examiner*—Hien Vo
*Attorney, Agent, or Firm*—Wolf, Greenfield & Sacks, P.C.

[57] ABSTRACT

The time period that a foot is in contact with the ground during a stride taken by a user, and the period that the foot is not in contact with the ground between strides taken by the user are determined by processing and analyzing the output signal of an accelerometer. The accelerometer is mounted on the user such that its acceleration sensing axis senses acceleration in a direction substantially parallel to the bottom of the user's foot. The output of the accelerometer is high-pass filtered, amplified, and fed to the input of a micro-controller, which monitors the signal for positive and negative signal spikes that are indicative, respectively, of the moment that the foot of the user leaves the ground and the moment that the foot impacts with the ground. By measuring time intervals between these positive and negative spikes, average "foot contact times" and "foot loft times" of the user may be calculated. To derive the pace of the user, the average foot contact time is multiplied by a first constant if it is less than 400 milli-seconds (ms) and is multiplied by a second constant if it is greater than 400 ms. This pace value may, in turn, be used to calculate the distance traveled by the user.

59 Claims, 13 Drawing Sheets

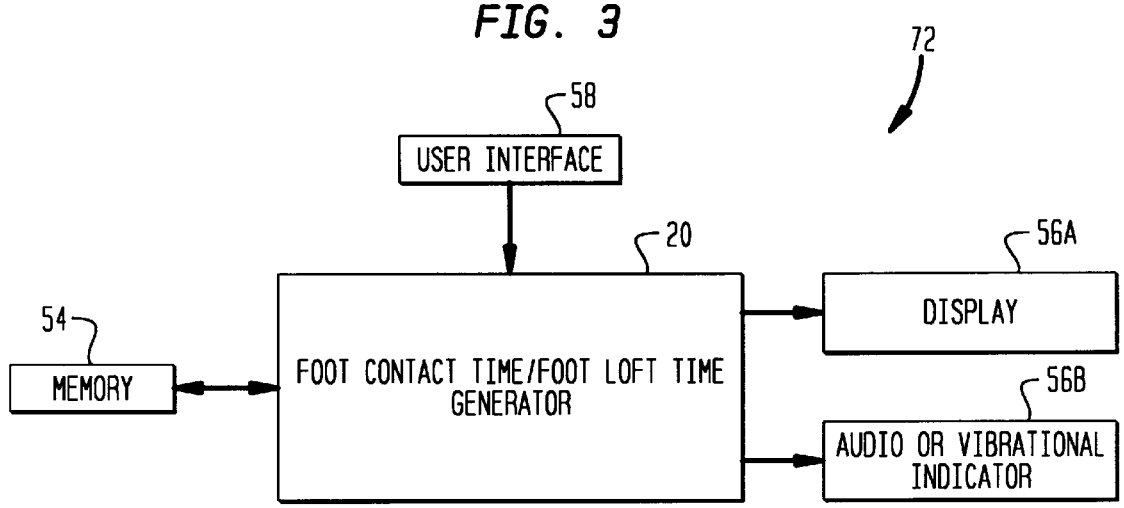
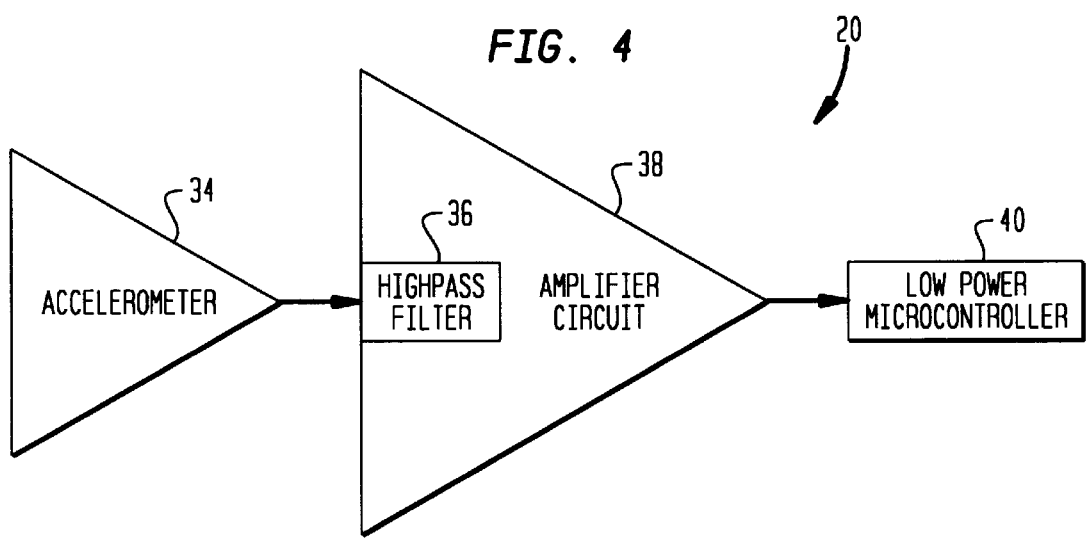

FIG. 7
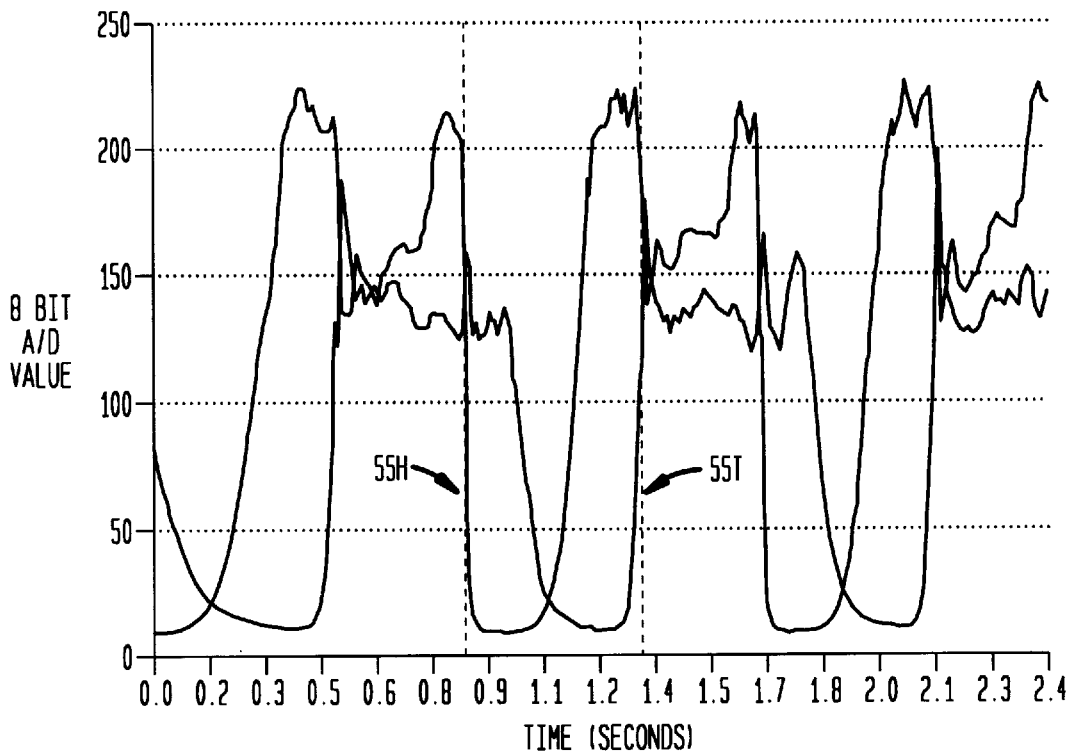
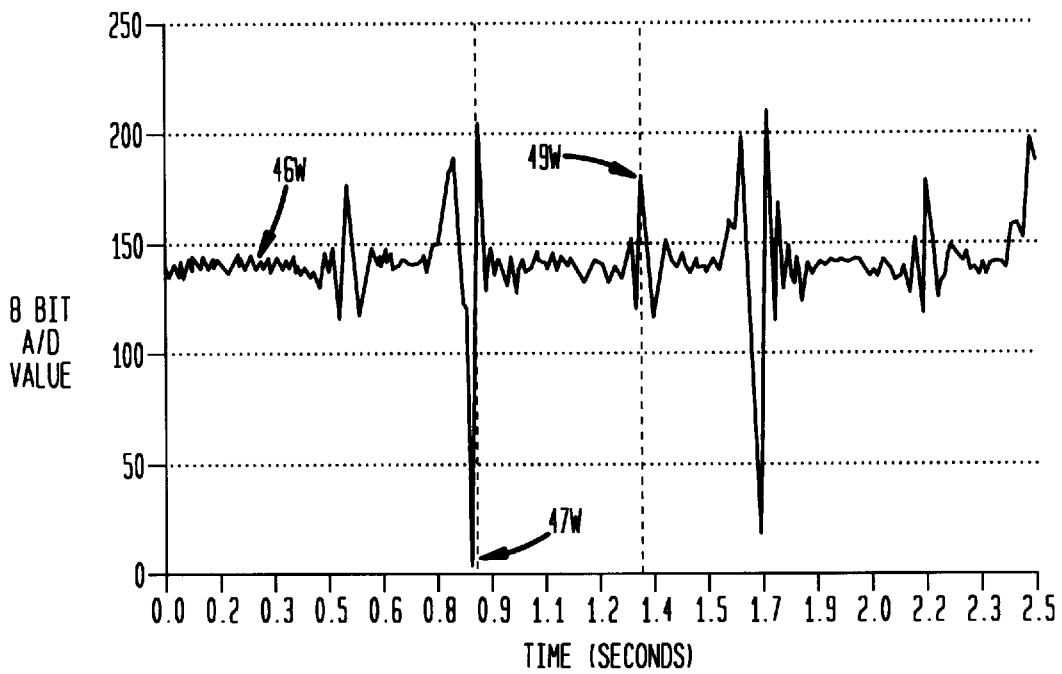

1

MEASURING FOOT CONTACT TIME AND FOOT LOFT TIME OF A PERSON IN LOCOMOTION

This is a continuation of application Ser. No. 08/942,802, filed Oct. 2, 1997.

BACKGROUND OF THE INVENTION

1. Field of the Invention

The present invention relates to the monitoring of the orthopedic motion of a person and, more particularly, to the measuring of foot contact time, foot loft time, speed and/or pace of a person in locomotion.

2. Discussion of the Related Art

It is known that useful information may be derived from the measurement of the "foot contact time" of a person in locomotion, wherein "foot contact time" refers to the period of time that a foot of a person is in contact with the ground during a stride taken by the person. Once the foot contact time of a person is known, other information, such as rate of travel, distance traveled and ambulatory expended energy may be calculated based upon this measured foot contact time.

In the past, foot contact time has been measured by placing pressure-sensitive sensors or switches, such as resistive sensors, in both the heel and toe portions of the sole of a shoe, and measuring a time difference between a first signal output by the heel sensor (which indicates that the foot has made physical contact with the ground) and a second signal output by the toe sensor (which indicates that the foot has left the ground). These sensors, however, are subjected to a high-impact environment inside of the shoe, and therefore fail frequently. In addition, inaccurate foot contact time measurements may result when a user is taking strides during which either the heel sensor or the toe sensor is not activated, for example, when a user is running on his or her toes.

Another device well-known in the art is a pedometer. A pedometer typically is mounted on the waist of a user and is configured to count the footsteps of the user by measuring the number of times the user's body moves up an down during footsteps taken by the user. A well-known prior art pedometer design uses a weight mounted on a spring to count the number of times that the user's body moves up and down as the user is walking. By properly calibrating the pedometer according to a previously measured stride length of the user, the distance traveled by the user may be measured by this device. These "weight-on-a-spring" pedometers, however, generally cannot measure the distance traveled by a runner because the weight experiences excessive bouncing during running and footsteps are often "double-counted" because of this bouncing, causing the pedometer to produce inaccurate results. These devices, therefore, may not be used across different training regimes (e.g., walking, jogging, and running).

Another prior art pedometer device uses an accelerometer to measure the number of times that a foot impacts the ground when a user is in locomotion. That is, an accelerometer is mounted on a shoe so as to produce a signal having pronounced downward going peaks that are indicative of moments that the foot impacts the ground. These devices therefore produce results similar to the prior art weight-on-a-spring pedometer devices in that they merely count the number of footsteps of a user, and must be calibrated according to the stride length of the user in order to calculate the distance traveled by the user. Thus, these accelerometer-based devices are subject to similar limitations as are the weight-on-a-spring devices, and are not able to measure the foot contact time of a user in locomotion.

It is therefore a general aim of the present invention to provide a new approach to pedometry that is affordable, reliable, easy to use and accurate.

SUMMARY OF THE INVENTION

According to one aspect of the present invention, a method for analyzing activity of a person in locomotion on foot on a surface involves using a sensor to generate a signal in response to movement of the person when the person is in locomotion without exerting compression forces on the sensor to generate the signal. The signal is analyzed to determine a moment that the foot leaves the surface during a footstep taken by the person.

According to another aspect of the invention, a device for analyzing activity of a person in locomotion on foot on a surface includes a sensor and a signal processor. The sensor is to be supported in relation to the foot, and is configured and arranged to provide an output signal in response to movement of the foot during at least one footstep taken by the person without requiring compression forces thereon to generate the signal. The signal processor is coupled to the sensor to receive the output signal therefrom, and is configured to analyze the output signal of the sensor to determine at least one moment that the foot leaves the surface during the at least one footstep.

According to another aspect of the invention, a method for monitoring activity of a person in locomotion on foot involves using a first electronic device to determine at least one foot contact time of the person. Information, which is based upon the at least one foot contact time, is transmitted from the first electronic device to a second electronic device via a wireless communication channel.

According to another aspect, a system for monitoring activity of a person in locomotion on foot includes first and second electronic devices. The first electronic device is to measure at least one foot contact time of the person. The second electronic device, which is coupled to the first electronic device via a wireless communication channel, receives information from the first electronic device which is based upon the at least one foot contact time measured by the first electronic device.

According to another aspect of the invention, a method for analyzing activity of a person in locomotion on foot on a surface involves mounting a sensor above a bottom surface of a foot of the person so that the sensor generates a signal in response to movement of the person when the person is in locomotion. The signal is analyzed to determine a moment that the foot leaves the surface during a footstep taken by the person.

According to another aspect of the invention, a device for analyzing activity of a person in locomotion on foot on a surface includes a sensor and a signal processor. The sensor is to be supported by the person above a bottom surface of a foot of the person, and is configured and arranged to provide an output signal in response to movement of the foot during at least one footstep taken by the person. The signal processor is coupled to the sensor to receive the output signal therefrom, and is configured to analyze the output signal of the sensor to determine at least one moment that a foot of the person leaves the surface during the at least one footstep.

According to another aspect, a method for analyzing activity of a person in locomotion on foot on a surface involves using a sensor to generate a signal in response to movement of the person when the person is in locomotion without exerting compression forces on the sensor to generate the signal. The signal is analyzed to determine at least one foot contact time and/or at least one foot loft time of the person during at least one footstep taken by the person.

According to another aspect of the invention, a device for analyzing activity of a person in locomotion on foot on a surface includes a sensor and a signal processor. The sensor is configured and arranged to provide a signal in response to movement of a foot of the person during at least one footstep taken by the person without requiring compression forces thereon to generate the signal. The signal processor is coupled to the sensor to receive the signal therefrom, and is configured to determine at least one foot contact time and/or at least one foot loft time of the person during at least one footstep taken by the person.

According to another aspect of the invention, a method for analyzing activity of a person in locomotion on foot on a surface involves mounting a sensor above a bottom surface of a foot of the person so that the sensor generates a signal in response to movement of the person when the person is in locomotion. The signal is analyzed to determine at least one foot contact time and/or at least one foot loft time of the person during at least one footstep taken by the person.

According to yet another aspect, a device for analyzing activity of a person in locomotion on foot on a surface includes a sensor and a signal processor. The sensor is to be supported by the person above a bottom surface of a foot of the person, and is configured to generate a signal in response to movement of the person when the person is in locomotion. The signal processor is coupled to the sensor to receive the signal therefrom, and is configured to determine at least one of at least one foot contact time and at least one foot loft time of the person during at least one footstep taken by the person.

BRIEF DESCRIPTION OF THE DRAWINGS

FIG. 3 is a block diagram of a system in which the invention may be used;

FIG. 4 is a block diagram of one embodiment of a circuit according to the present invention;

FIG. 7 is a pair of graphs that compare the amplified/filtered output of the accelerometer according to the invention with data obtained using prior art resistive sensors during a period that a user is walking;

DETAILED DESCRIPTION OF THE INVENTION

Figure 1:
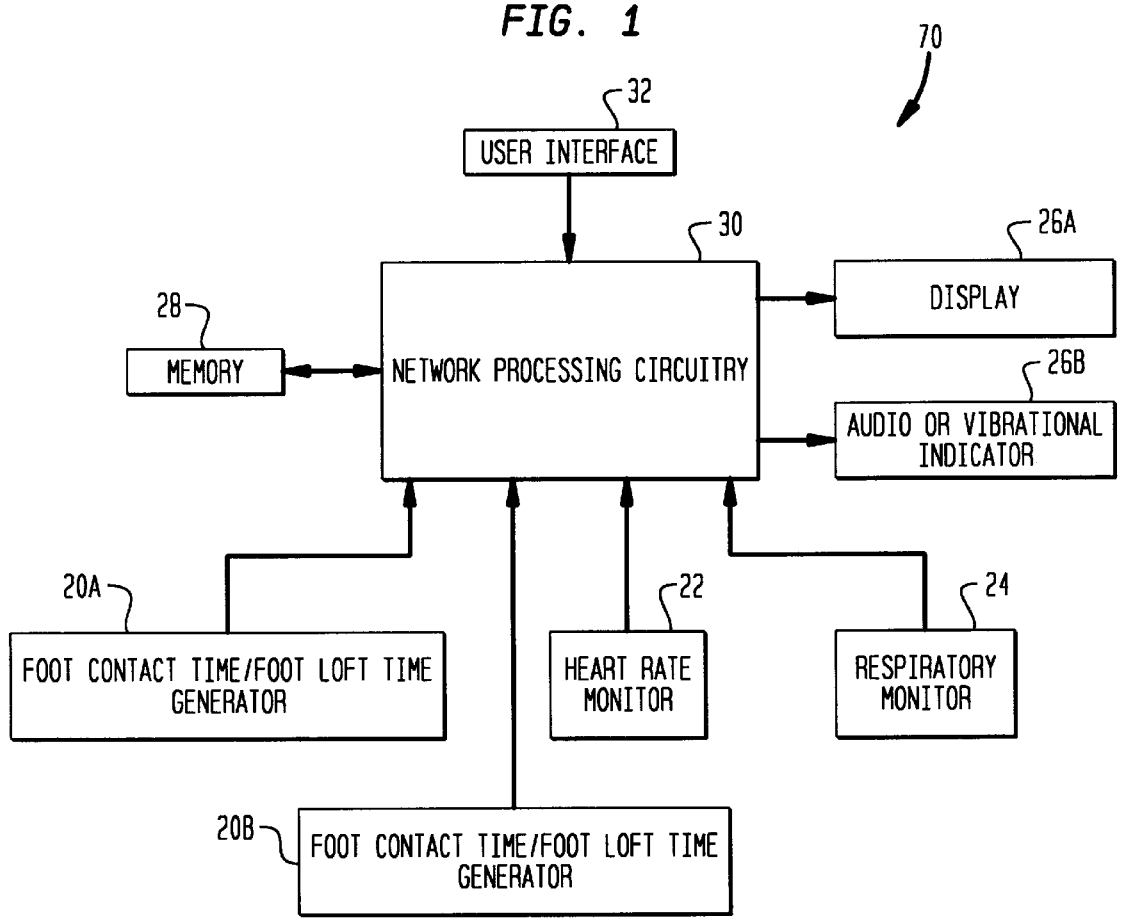
FIG. 1 is a block diagram of a network in which the present invention may be used.

FIG. 1 shows a block diagram of a network 70 in which the present invention may be used. As shown, network 70 includes network processing circuitry 30, a memory unit 28, a user interface 32, a display 26A, and an audio or vibrational indicator 26B. Network processing circuitry 30 also is coupled to receive inputs from one or more monitoring devices, such as foot contact time/foot loft time generators 20A and 20B, heart rate monitor 22, and respiratory monitor 24. The devices shown in FIG. 1 may be linked together, for example, via direct wiring or capacitive coupling, by using radio-frequency (RF) or infa-red (IR) transmitters/receivers, or by any other information transmission medium known to those skilled in the art.

Network processing circuitry 30 may include a personal computer, or any other device capable of processing information from the various inputs of network 70. Memory unit 28 is coupled to network processing circuitry 30 and is used to store programming and data for network processing circuitry 30 and/or to log data processed by circuitry 30. User interface 32 also is coupled to network processing circuitry 30 and permits a user, e.g., a walker, jogger or runner, to select a particular feature implemented by operation of a software routine, to input particular operating parameters, or to select particular outputs for display 26A and/or audio or vibrational indicator 26B. Heart rate monitor 22 and respiratory monitor 24 operate according to known methods and supply inputs to network processing circuitry 30.

Each one of foot contact time/foot loft time generators 20A and 20B operates according to the present invention and supplies a separate input to network processing circuitry 30. By receiving information from the outputs of foot contact time/foot loft time generators 20A and 20B, heart rate monitor 22, and respiratory monitor 24, as well as inputs from any other type of electronic health monitoring device, network processing circuitry 30 is able to process all such information and provide a user with a fitness metric, to help the user attain a peak fitness level in the most efficient manner possible, or other health related information, useful for physical therapy, recovery, etc.

Figure 2:
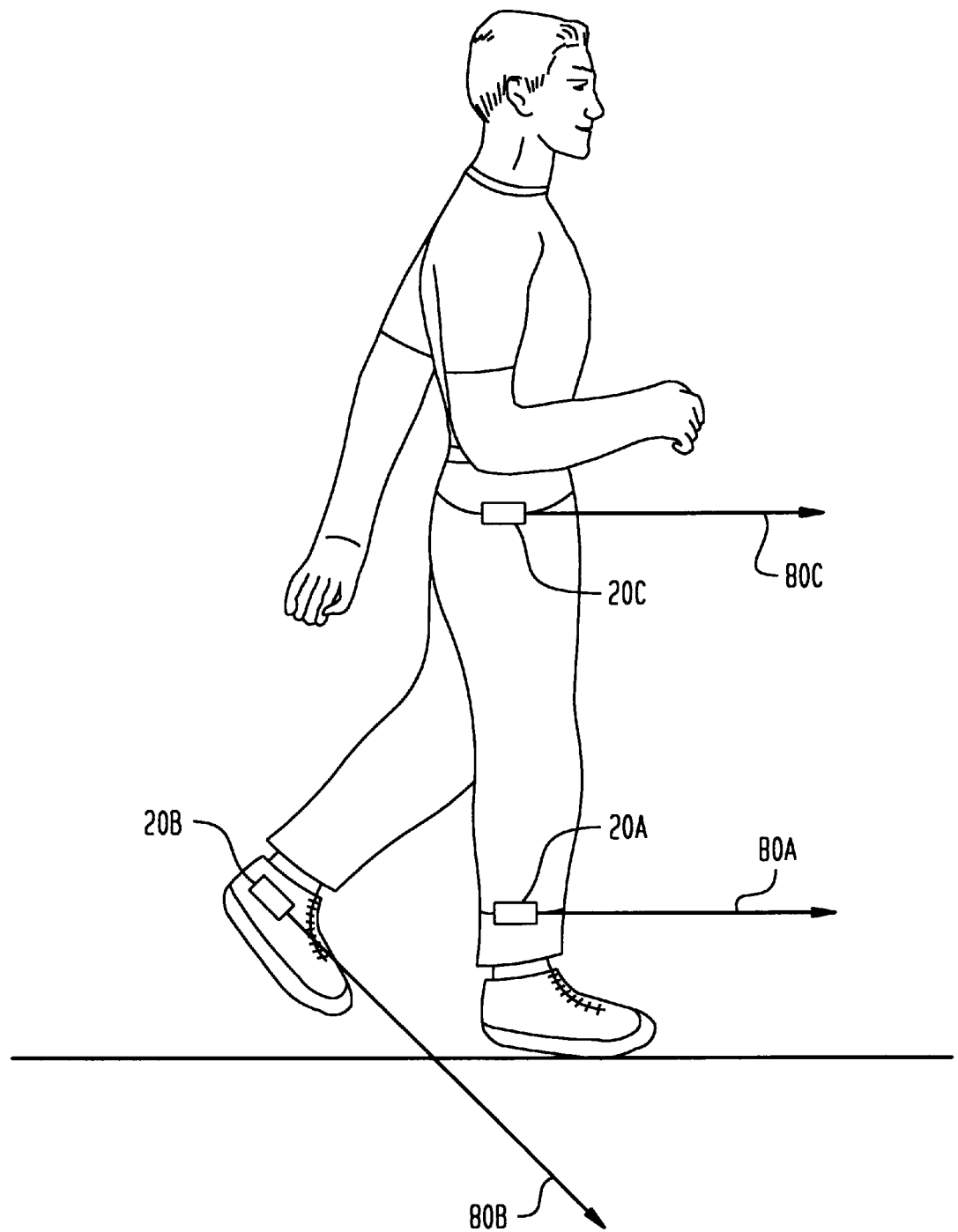
FIG. 2 is an illustration showing how the invention may be mounted with respect to a user.

FIG. 2 illustrates how a device according to the invention may be mounted on a user. Each of devices 20A–20C shown in FIG. 2 has a particular axis in which it senses acceleration, i.e., an acceleration sensing axis. According to one embodiment of the invention, each of the devices should be mounted such that the acceleration sensing axis of the device is oriented substantially parallel to a bottom surface of the foot of the user. For example, device 20A is mounted on the ankle of the user, device 20B is mounted on or within the shoe of the user, and device 20C is mounted on the waist of the user, with the acceleration sensing axises of the devices being oriented as indicated by arrows 80A, 80B and 80C, respectively. In each case, this positioning of the acceleration sensing axis has been found to produce an output signal that is most strongly indicative of both: (1) the moment at which the foot of the user leaves the surface, and (2) the moment at which the foot of the user comes into contact with the surface. It is hypothesized that this is true because a large portion of the change in acceleration sensed by the device is caused by the friction between the shoe of the user and the surface, rather than being caused primarily by the impact of the shoe with the surface, as is the case with prior art accelerometer-based pedometers.

FIG. 3 shows a system 72 according to the present invention. As shown, the system 72 includes a foot contact time/foot loft time generator 20 (which could correspond to either of foot contact time/foot loft time generators 20A and 20B in FIG. 1), a memory unit 54, a user interface 58, a display 56A, and an audio or vibrational indicator 56B. According to one embodiment, foot contact time/foot loft time generator 20 includes a micro-controller having virtually all circuitry, e.g., memory, timers and analog-to-digital (A/D) converters, on board, so that memory unit 54 need only be used to perform functions such as permanently storing data produced by foot contact time/foot loft time generator 20.

User interface 58 may be activated conventionally by means of buttons, switches or other physically actuated devices, or may be voice activated using a commercially available voice activation device. As discussed in more detail below, user interface 58 may be used, for example: (1) to adjust any of several parameters used in a software routine according to the invention, (2) to select any of several possible outputs for the user, e.g., outputs could be displayed on display 56A or could provide a user with an audio or vibrational indication via audio or vibrational indicator 56B, or (3) to select features which are implemented through software routines called automatically responsive to user inputs.

FIG. 4 shows an exemplary embodiment of the foot contact time/foot loft time generator 20 shown in FIG. 3. As shown, foot contact time/foot loft time generator 20 includes an accelerometer 34, an amplifier circuit 38 (which has a high-pass filter 36 included within it), and a micro-controller 40. An output of accelerometer 34 is connected to an input of amplifier circuit 38, and an output of amplifier circuit 38 is connected to an input of micro-controller 40.

Figure 5:
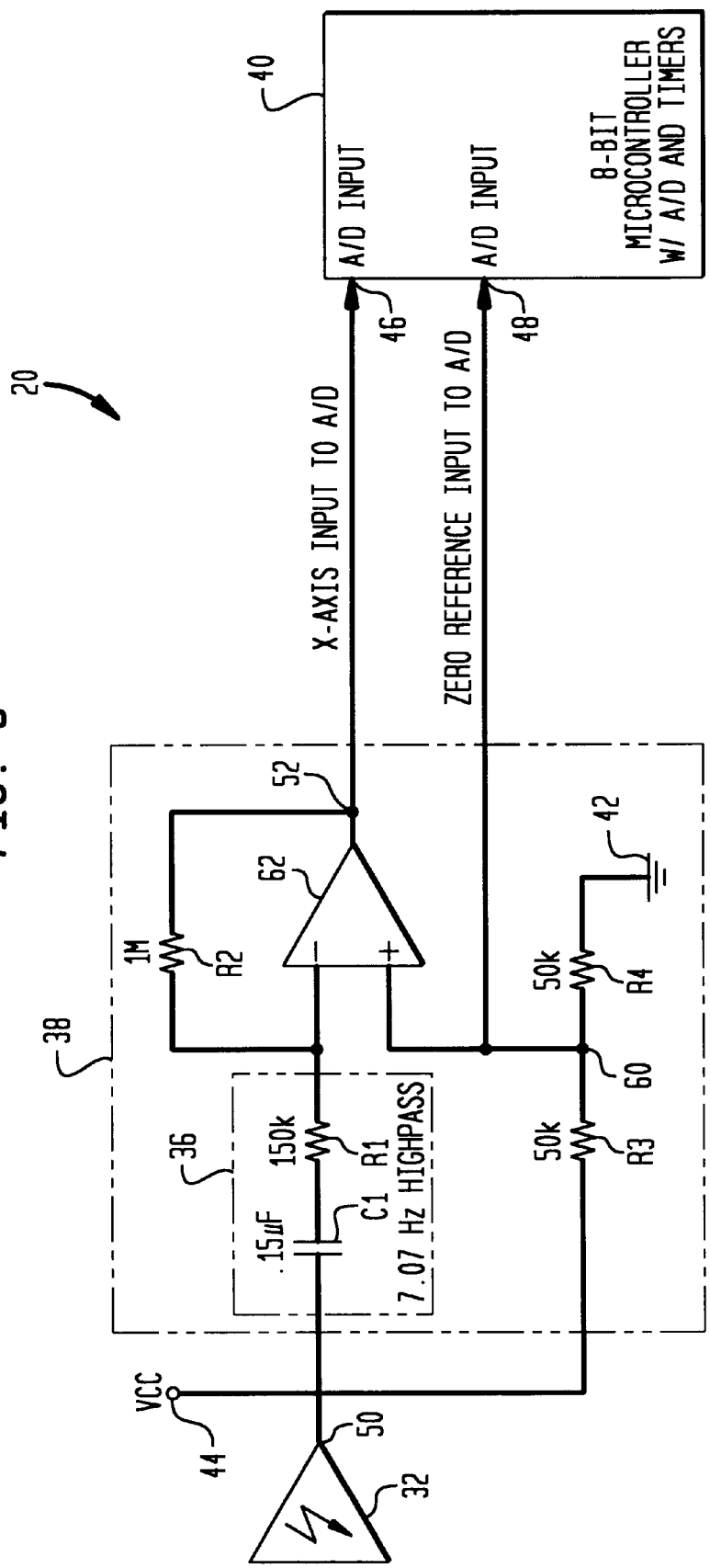
FIG. 5 is a schematic diagram of the circuit shown in FIG. 4.

FIG. 5 shows the foot contact time/foot loft time generator 20 shown in FIG. 4 in more detail. As shown in FIG. 5, output 50 of accelerometer 32 is provided to an input capacitor C1 included in amplifier circuit 38. Amplifier circuit 38 further includes operational amplifier 62 and resistors R1–R4. According to one embodiment, accelerometer 32 may comprise part number ADXL250, manufactured by Analog Devices, Inc., and operational amplifier 62 may comprise part number MAX418 produced by MAXIM, Inc.

As shown in FIG. 5, resistor R1 is connected between input capacitor C1 and the inverting input of operational amplifier 62, and resistor R2 is connected in feedback between the inverting input terminal and output 52 of operational amplifier 62. Thus, the combination of input capacitor C1 and resistor R1 form a high-pass filter, and the position of resistors R1 and R2 place the amplifier circuit in an inverting configuration with a gain-factor dependent on the relative values of resistors R1 and R2. In the embodiment shown, resistor R2 has a value of one mega-ohm and resistor R2 has a value of 150 kili-ohms, so that the gain factor of the amplifier is approximately (−6.6). In addition, according to the embodiment shown, capacitor C1 has a value of 0.15 microfarads, so that high-pass filter section 36 of amplifier circuit 38 cuts off input signal frequencies that are less than approximately 7.07 hertz.

Resistor R3 is connected between VCC supply node 44 and the non-inverting input 60 of operational amplifier 62, and resistor R4 is connected between non-inverting input 60 and ground node 42. VCC supply node 44 is maintained at approximately 5 volts (e.g., regulated from a six-volt battery) in relation to ground node 42, and resistors R3 and R4 are of equal values (e.g., 50 kili-ohms each) so that the voltage at non-inverting input node 60 is maintained approximately midway between the voltage at VCC supply node 44 and ground (i.e., approximately 2.5 volts).

Output 52 of amplifier circuit 38 is connected to a first A/D input 46 of low-power micro-controller 40, and node 60 of amplifier circuit 38 is connected to a second A/D input 48 of micro-controller 40. According to one embodiment, micro-controller 40 may comprise part number PIC:16C73 manufactured by Microchip, Inc. This micro-controller includes on-board memory, A/D converters, and timers. A/D input 48 of micro-controller 40 serves as a zero-reference that is maintained at approximately 2.5 volts (as described above), and input 46 of micro-controller 40 serves as a variable input that fluctuates between 0 and 5 volts. Micro-controller 40 samples the voltages at inputs 46 and 48 at a rate of approximately 500 samples-per-second, converts these samples into 8-bit unsigned digital values, and calculates the difference between the voltages at the two inputs, which difference is used during operation of software routines described in more detail below.

Figure 6:
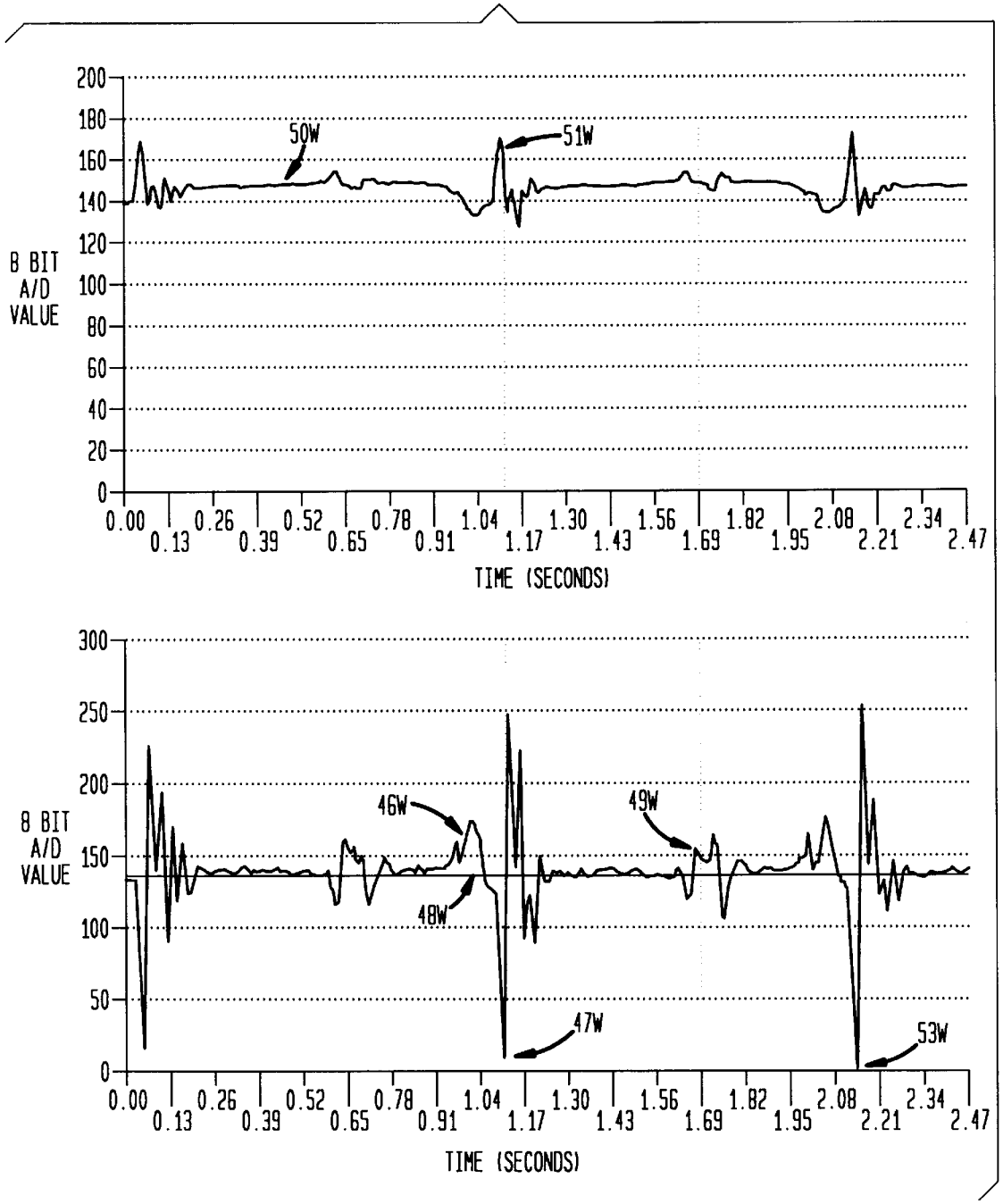
FIG. 6 is a pair of graphs showing signals at two nodes of the circuit shown in FIG. 5 during a period in which a user is walking.

FIG. 6 shows two curves along the same time axis. These curves represent the 8-bit unsigned digital values of the voltages at nodes 50 and 52 of the circuit shown in FIG. 5 during a period when a user is walking. That is, curve 50W in FIG. 6 represents (digitally) the voltage at output 50 of accelerometer 32 before it is filtered and amplified, and curves 46W and 48W, respectively, represent (digitally) the voltages at inputs 46 and 48 of micro-controller 40 during the period when the user is walking. While each of curves 46W, 48W and 50W shares a common time axis, the voltage-magnitude axis of curves 46W and 48W is distinct from the voltage-magnitude axis of curve 50W. Therefore, the placement of curve 50W above curves 46W and 48W is not intended to signify that curve 50W attains a higher amplitude than do curves 46W and 48W.

As shown in FIG. 6, because amplifier circuit 38 is configured to have a negative gain-factor, high peak 51W of curve 50W corresponds with low peak 47W of curve 46W. High peak 49W of curve 46W, however, does not appear to correspond to a low peak of curve 50W. That is, high peak 49W is ascertainable only after the output of accelerometer 34 has been high-pass filtered and amplified by amplifier circuit 38. It is high peak 49W in curve 46W that indicates the moment that the foot of the user has left the surface when the user is in locomotion.

Similarly, low peak 47W in curve 46W indicates the moment that the foot of the user has impacted with the surface when the user is in locomotion. By measuring the time difference between peak 47W and peak 49W of curve 46W, the foot contact time of the user when the user is in locomotion may be ascertained. As used herein, "foot contact time" refers to the period of time between when a foot of a user impacts a surface and when the foot next leaves the surface.

In a similar manner, the foot loft time of a user in locomotion may be determined. That is, by measuring the time difference between high peak 49W and low peak 53W in curve 46W, the foot loft time of the user is ascertainable. As used herein, "foot loft time" refers to the period of time between when a foot of a user leaves a surface and when the foot next comes into contact with the surface.

FIG. 7 shows the correspondence, when a user is walking, between (1) two curves 55H and 55T produced by resistive sensors mounted in the heel and toe, respectively, of a shoe and (2) the amplified and filtered output of the accelerometer according to the invention. That is, curve 55H represents the output of a resistive sensor mounted in the heel of a shoe, curve 55T represents the output of a resistive sensor mounted in the toe of the shoe, and curve 46W represents the voltage at node 52 of circuit 20 (shown in FIG. 5). All of these measurements were taken while a user was walking. While each of curves 55H, 55T and 46W shares a common time axis, the voltage-magnitude axis of curves 55H and 55T is distinct from the voltage-magnitude axis of curve 46W. Therefore, the placement of curves 55H and 55T above curve 46W is not intended to signify that curves 55H and 55T attain higher amplitudes than does curve 46W.

As shown by the dashed lines in FIG. 7, the high to low transition of curve 55H (which indicates that the shoe of the user has impacted with the ground) corresponds with low peak 47W of curve 46W, and the low-to-high transition of curve 55T (which indicates that the shoe of the user has left the ground) corresponds with high peak 49W of curve 46W. Thus, the foot contact time and foot loft time measurements that are obtained, when a user is walking, by measuring time differences between high and low peaks, and vice-versa, of the high-pass filtered/amplified output of an accelerometer (mounted as described above) appear to produce results that are at least as accurate as those produced by prior art resistive sensors.

Figure 8:
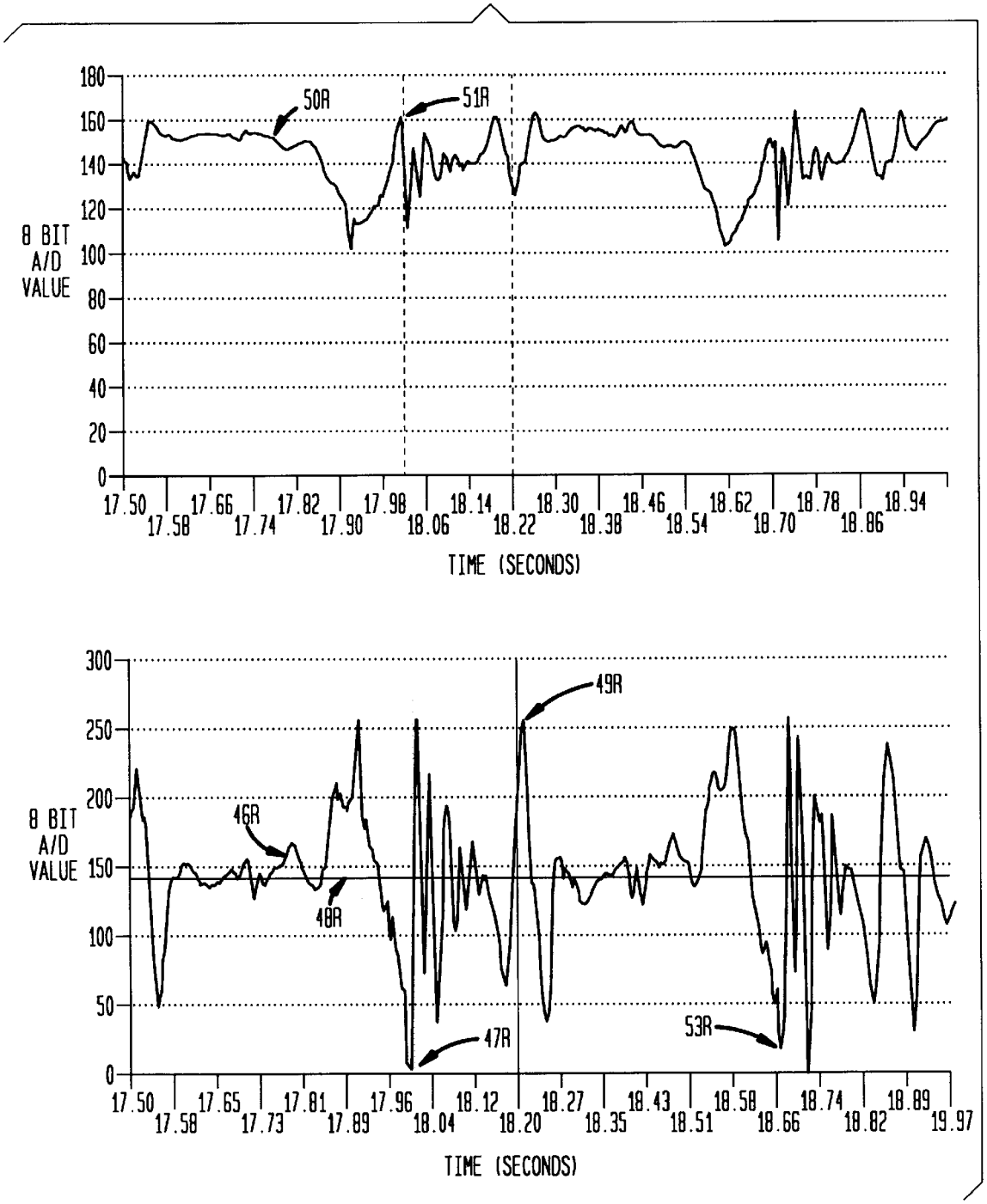
FIG. 8 is a pair of graphs showing signals at two nodes of the circuit shown in FIG. 5 during a period in which a user is running.

FIG. 8 shows two curves representing the 8-bit unsigned digital values of the voltages at nodes 50 and 52 of the circuit shown in FIG. 5 during a period when a user is running. That is, curve 50R in FIG. 8 represents the voltage at output 50 of accelerometer 32 before it is filtered and amplified, and curves 46R and 48R, respectively, represent the voltages at inputs 46 and 48 of micro-controller 40 during the period when the user is running. While each of curves 46R, 48R and 50R shares a common time axis, the voltage-magnitude axis of curves 46R and 48R is distinct from the voltage-magnitude axis of curve 50R. Therefore, the placement of curve 50R above curves 46R and 48R is not intended to signify that curve 50R attains a higher amplitude than do curves 46R and 48R.

As shown in FIG. 8, because amplifier circuit 38 is configured to have a negative gain-factor, high peak 51R of curve 50R corresponds with low peak 47R of curve 46R. High peak 49R of curve 46R. However, does not appear to correspond to a low peak of curve 50R. That is, high peak 49R is ascertainable only after the output of accelerometer 34 has been high-pass filtered and amplified by amplifier circuit 38. It is high peak 49R in curve 46R that indicates the moment that the foot of the user has left the ground when the user running.

Similarly, low peak 47R in curve 46R indicates the moment that the foot of the user has impacted with the ground when the user is running. By measuring the time difference between low peak 47R and high peak 49R of curve 46R, the foot contact time of the user, when the user is running, may be ascertained. In a similar manner, the foot loft time of the user may be determined. That is, by measuring the time difference between high peak 49R and low peak 53R in curve 46R, the foot loft time of the user, when the user is running, may be ascertained.

Figure 9:
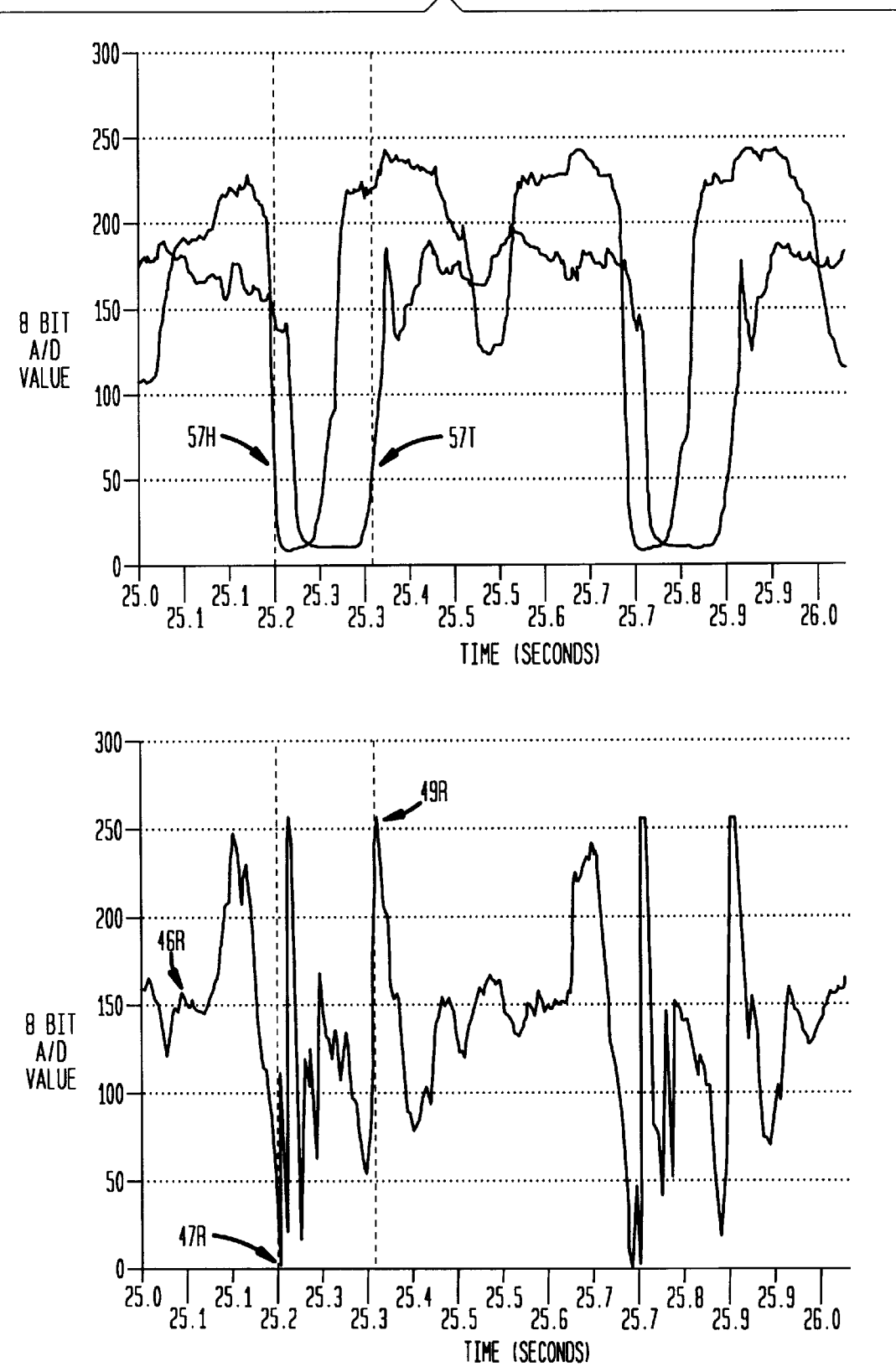
FIG. 9 is a pair of graphs that compare the amplified/filtered output of the accelerometer according to the invention with data obtained using prior art resistive sensors during a period that a user is running.

FIG. 9 shows the correspondence, when a user is running, between (1) two curves 57H and 57T produced by resistive sensors mounted in the heel and toe, respectively, of a shoe and (2) the amplified and filtered output of the accelerometer according to the invention. That is, curve 57H represents the output of a resistive sensor mounted in the heel of a shoe, curve 57T represents the output of a resistive sensor mounted in the toe of the shoe, and curve 46R represents the voltage at node 52 of circuit 20 (shown in FIG. 5). All of these measurements were taken while a user was running. While each of curves 57H, 57T and 46R shares a common time axis, the voltage-magnitude axis of curves 57H and 57T is distinct from the voltage-magnitude axis of curve 46R. Therefore, the placement of curves 57H and 57T above curve 46R is not intended to signify that curves 57H and 57T attain higher amplitudes than does curve 46R.

As shown by the dashed lines in FIG. 9, the high-to-low transition of curve 57H (which indicates that the shoe of the user has impacted with the ground) corresponds with low peak 47R of curve 46R, and the low-to-high transition of curve 57T (which indicates that the shoe of the user has left the ground) corresponds with high peak 49R of curve 46R. Thus, the foot contact time and foot loft time measurements that are obtained, when a user is running, by measuring time differences between high and low peaks, and vice-versa, of the high-pass filtered/amplified output of an accelerometer (mounted as described above) appear to produce results that are at least as accurate as those produced by prior art resistive sensors.

The output signal from accelerometer 34 (shown in FIGS. 4 and 5) is analyzed by micro-controller 40 using two primary software routines: (1) a continuous-loop routine that accumulates data, e.g., foot contact times and foot loft times, pursuant to each iteration of the loop, and (2) and an interrupt routine that interrupts the continuous-loop routine and analyzes the data that has been accumulated by the continuous-loop routine at the time the interrupt is initiated. These routines may be written in any software language and preferredly are stored in the on-board memory (not shown) of micro-controller 40 (shown in FIGS. 4 and 5). These routines could be user initiated or, preferredly, are initiated automatically upon power-up of micro-controller 40. The particular steps performed by each of these primary software routines are described in detail below.

Referring briefly back to FIG. 5, because the voltage at each of inputs 46 and 48 of micro-controller 40 is converted to an 8-bit digital word, the amplitude of the voltage at each input will be represented as one of 256 discrete levels. Also, because resistors R3 and R4 create a voltage at node 60 that is approximately half-way between the high-supply voltage of five volts and the ground, i.e., approximately 2.5 volts, the zero reference at input 48 will remain near the midpoint of the 256 levels, i.e., at approximately level 128.

Figure 10:
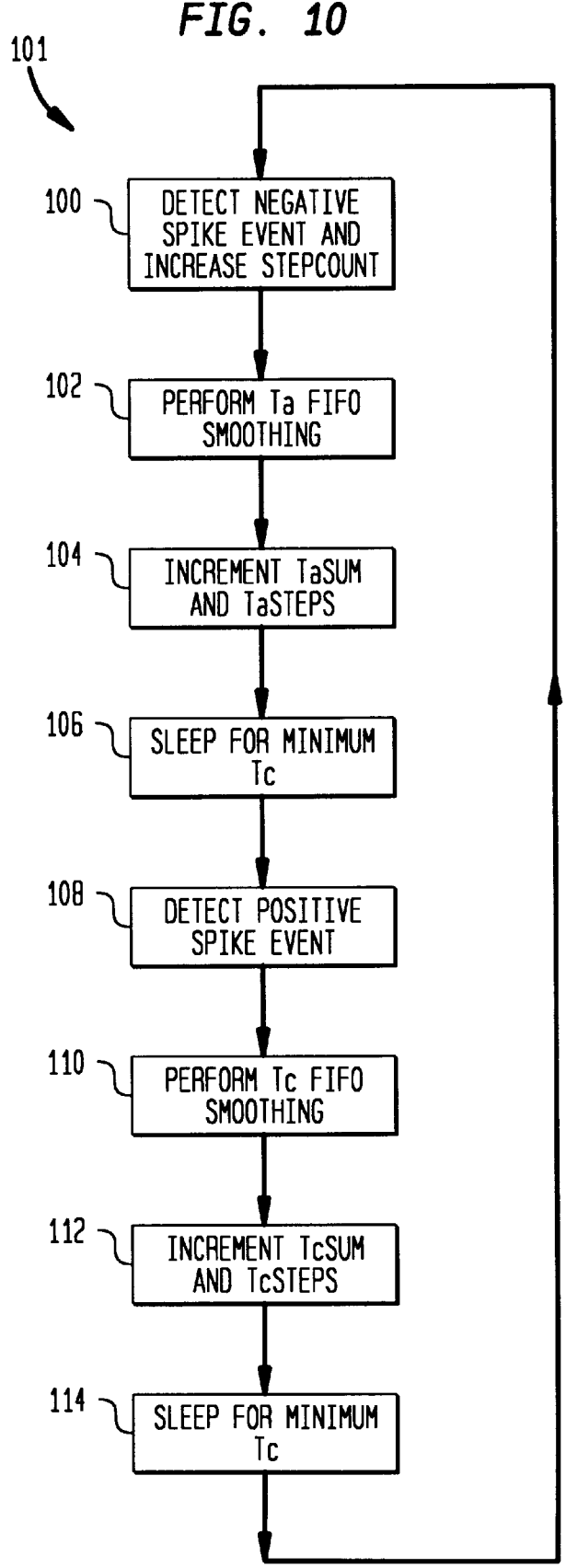
FIG. 10 is a high-level flow diagram of a continuous-loop portion of a method for measuring foot contact time according to the invention.

Referring now to FIG. 10, a high-level flow chart of the continuous-loop routine performed by micro-controller 40 (shown in FIG. 5) is shown. Essentially, continuous-loop portion 101 continuously monitors the voltage across inputs 46 and 48 of micro-controller 40 to determine when negative and positive voltages differences (between inputs 46 and 48) in excess of predetermined thresholds occur. These negative and positive voltage differences are indicative, respectively, of the foot of a user impacting with and leaving the ground.

As shown in FIG. 10, continuous-loop 101 includes steps 100, 102, 104, 106, 108, 110, 112 and 114. Many of these high-level steps include several lower-level sub-steps, which will be described in detail below in connection with the description of FIG. 12.

During step 100 of loop 101, micro-controller 40 continuously monitors the voltages at inputs 46 and 48 to determine when the voltage at input 46 falls to more than a particular voltage below the voltage at input 48. According to one embodiment, a voltage at input 46 that is more than 50 levels (of the 256 possible voltage levels) lower than the zero reference level at input 48 is considered a "negative spike event" and the software assumes that the user's foot has impacted with the ground at the moment the negative spike event occurs. The occurrence of a negative spike event causes an "air time" (Ta) timer in micro-controller 40 to stop and a "contact time" (Tc) timer to start. The time measured by the air time (Ta) timer represents the time difference between the last "positive spike event" (defined below) and the negative spike event just detected. When a negative spike event occurs, a "StepCount" value, i.e., a counted number of footsteps of the user, also is increment.

Next, during step 102, the three most recent air times (i.e., air time (Ta) values), which were calculated previously and stored in memory, are subjected to a technique known as FIFO smoothing, which serves to eliminate air time (Ta) measurements that appear to be erroneous. The routine used to perform this FIFO smoothing is described in detail below.

During step 104, a running total of air time (Ta) values (TaSum) is incremented by the most recently available air time (Ta) value and the total number of air time (Ta) values included in the current TaSum value (TaSteps) is incremented by one. These values are maintained so that an average air time (Ta) value (TaAverage) may eventually be calculated by dividing the TaSum value by the TaSteps value.

During step 106, which is performed after steps 100, 102 and 104 are performed, the system "sleeps" for a period of time equal to a minimum possible foot contact time (Tc) for a user, e.g.. 122 milli-seconds (ms), so that the system will not think that any positive spikes occurring during this sleep period are a positive spike event (defined below).

Steps 108, 110, 112 and 114 are similar to steps 100, 102, 104, and 106, respectively, except that a foot contact time (Tc), rather than an air time (Ta), is determined.

During step 108 of loop 101, micro-controller 40 continuously monitors inputs 46 and 48 for a particular voltage difference therebetween. According to one embodiment, a positive voltage at input 46 that is more than 10 levels (of the 256 possible voltage levels) greater than the zero reference level at input 48 is considered a "positive spike event" and the software assumes that the users foot has left the ground at the moment the positive spike event occurs. The occurrence of a positive spike event causes the contact time (Tc) timer to stop and causes the air time (Ta) timer to start. The time measured by the contact time (Tc) timer represents the time difference between the last negative spike event and the positive spike event just detected.

During step 110, the three most recent contact time (Tc) times, which were calculated previously and stored in memory, are subjected to FIFO smoothing, which serves to eliminate foot contact time (Tc) measurements that appear to be erroneous.

During step 112, a running total of contact time (Tc) values (TcSum) is incremented by the most recently available contact time (Tc) value and the total number of contact time (Tc) values included in the current TcSum value (TcSteps) is incremented by one. These values are maintained so that an average contact time (Tc) value (TcAverage) may be calculated eventually by dividing the TcSum value by the TcSteps value.

During step 114, which is performed after steps 108, 110 and 112 are performed, the system "sleeps" for a period of time equal to a minimum possible foot contact time for a user so that the system will not think that any negative spikes occurring during this sleep period constitute a negative spike event. After the sleep period of step 114, the routine returns to step 100 and loop 101 repeats continuously until an interrupt (discussed below) is detected.

Figure 11:
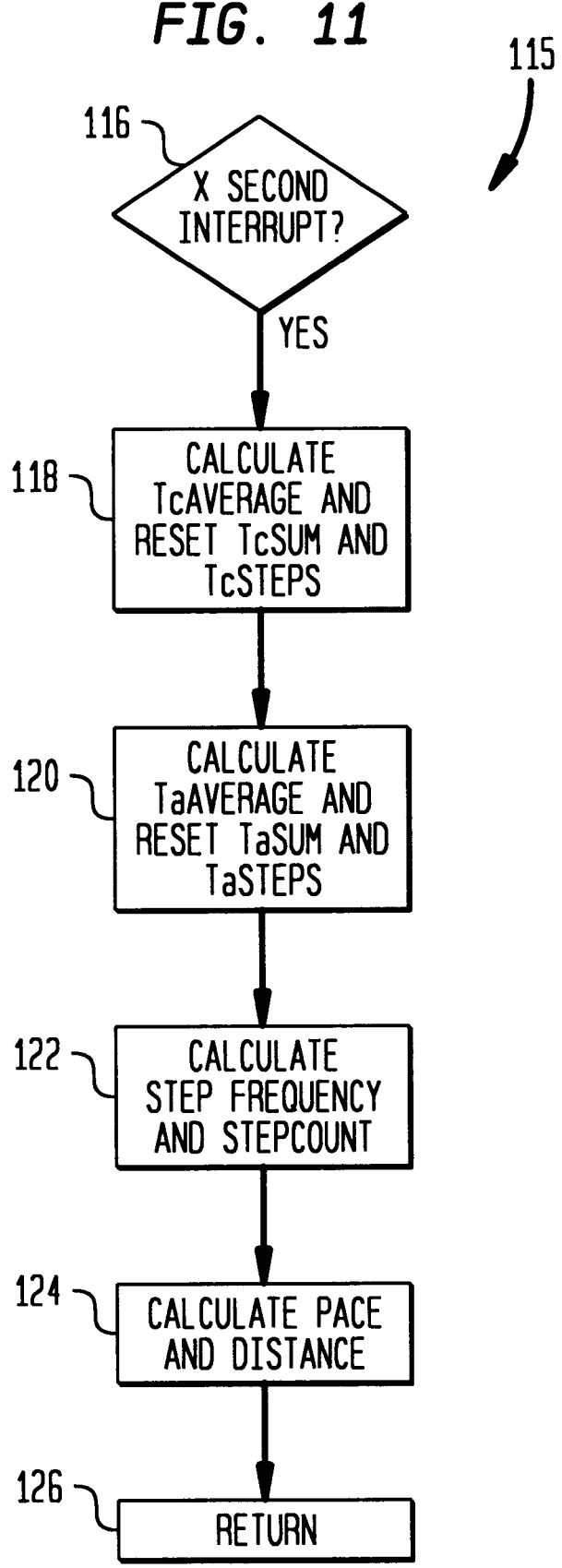
FIG. 11 is a high-level flow diagram of an interrupt portion of the method for measuring foot contact time according to the invention.

Referring now to FIG. 11 a high-level interrupt routine 115 now will be briefly explained, with a more detailed description of each high-level step and its associated lower-level sub-steps following below in connection with the description of FIG. 13.

Interrupt routine 115 may programmed to run at any given time interval, but preferredly should not be run any more frequently than once every two seconds so that meaningful data may be gathered by loop 101 before such data is evaluated by routine 115.

Step 116 of interrupt routine 115 causes the routine to interrupt continuous-loop 101. Next, step 118 calculates the average contact time (Tc) value (TcAverage) over several steps of a user and resets the TcSum and TcSteps values in loop 101 to zero. Similarly, step 120 calculates the average air time (Ta) value (TaAverage) and resets the TaSum and TaSteps values in loop 101 to zero.

In step 122, the step frequency of the user is determined (in a manner described below) based on the calculated TcAverage and TaAverage values, and the total number of steps of the user is calculated by multiplying the StepCount value from loop 101 by two.

Next, in step 124, the pace of the user is calculated according to an algorithm described below, and the distance traveled by the user is calculated according to an equation (described below) that uses both the calculated pace value and the time period in which the pace value was determined as variables. This distance measurement could be cumulative of past distance measurements to determine a total distance traveled. The cumulative distance value therefore would be resettable by the user so that the user could measure distance traveled from a zero reference point.

Finally, after the calculations in step 124, or any other desired calculations, are performed, step 126 returns interrupt routine 115 to the continuous-loop 101 for further measurements of contact time (Tc) and air time (Ta) values.

Figure 12:
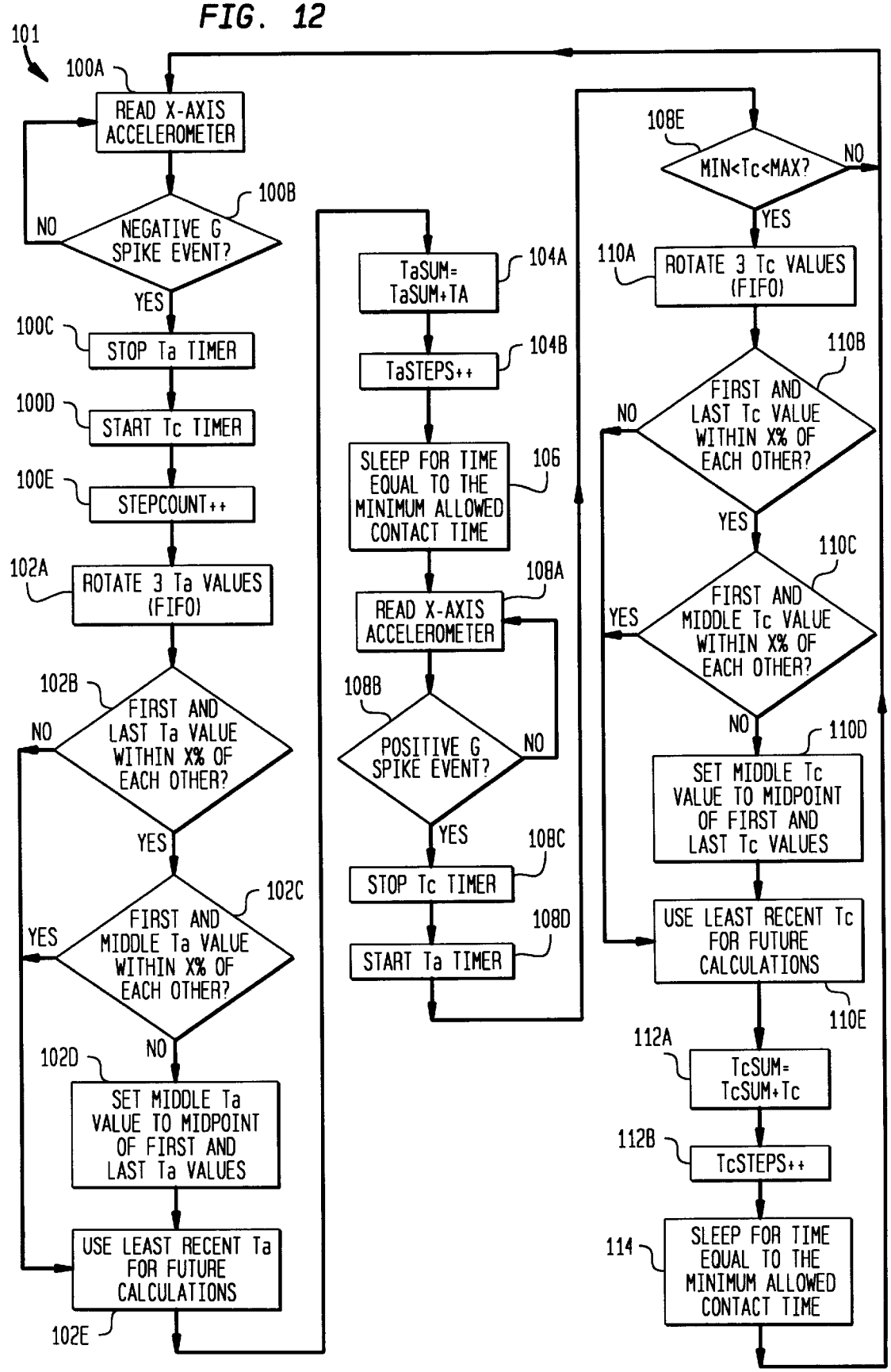
FIG. 12 is a more detailed flow diagram of the continuous-loop portion of the method shown in FIG. 10.

FIG. 12 shows a lower-level flow chart of continuous-loop 101. As shown, high-level step 100 (shown in FIG. 10) includes five lower-level sub-steps 100A–100E.

In steps 100A and 100B, the analog voltages at inputs 46 and 48 of micro-controller 40 are sampled (in step 100A) until a negative spike event is detected (in step 100B) in the voltage at input 46 that is indicative of the foot of a user impacting with the ground. According to one embodiment, the analog voltages at inputs 46 and 48 are sampled until the voltage at input 46 falls to less than 50 levels (of a possible 256 discrete voltage levels) below the level of reference input 48, which should remain approximately at level 128 (i.e., at approximately 2.5 volts on a 5-volt scale). 50 levels corresponds to approximately 0.98 volts on a 5-volt scale. This sampling is done at a rate of 500 samples per second.

The reference level at input 48 may float up or down slightly due to temperature variations of the amplifier circuit, etc. But, because any changes in the reference level at input 48 caused by external factors (such as temperature variations) likely will correspond to changes in the signal level at input 46 due to these factors, the difference between the voltages at nodes 46 and 48 should be affected only by the fluctuating signal generated by the accelerometer, and should not be affected by changes in the operating conditions of the circuit.

Once a negative spike event is detected in step 100B, an air time (Ta) timer is stopped (in step 100C) and a foot contact time (Tc) timer is started (in step 100D). The air time (Ta) timer would have been started responsive to the detection of a positive spike event (described below), which is indicative of the foot of the user leaving the ground, during a previous loop of continuous-loop routine 101. Thus, the air time (Ta) timer, when stopped in step 100C, provides a measurement of the air time between footsteps of the user, i.e., the time period between when the foot of the user last left the ground (i.e., the last positive spike event) and when the foot most recently impacted with the ground (i.e., the negative spike event just detected).

In addition, in response to the detection of the negative spike event, the value of the variable StepCount is increased by one (in step 100E). The variable StepCount is reset prior to the user beginning a training regime so that its running total accurately measures the number of footsteps taken by one foot of the user during the training period.

After updating the variable StepCount (in step 100E), continuous-loop 101 proceeds to steps 102A–102E, which are included in "FIFO smoothing" step 100 of the high-level routine shown in FIG. 10. During steps 102A–102E, the three most recent values of air time, i.e., the three most recent air time (Ta) values, which have been stored in memory, are analyzed as follows.

First, during step 102A, the three most recent air time (Ta) values (from prior iterations of loop 101) are shifted to account for the newly-acquired air time (Ta) value (in step 100C). Specifically, the existing third most recent air time (Ta) value is discarded, the existing second most recent air time (Ta) value becomes the new third most recent value, the existing first most recent value becomes the new second most recent value, and the newly-acquired air time (Ta) value becomes the new first most recent air time (Ta) value.

Next, in steps 102B and 102C, the three most recent air time (Ta) values (after being shifted in step 102A) are compared, as described below, to ascertain whether the middle air time (Ta) value (i.e., the second most recent air time (Ta) value) appears to be anomalous. An anomalous air time (Ta) measurement (i.e., an anomalous air time (Ta) value) might occur, for example, when a user steps on a rock or slips on water or ice during a footstep. If the second most recent air time (Ta) value appears to be the result of an erroneous measurement, then (in step 102D) it is replaced with an average of the first and third most recent air time (Ta) values. Thus, because only the third most recent air time (Ta) value is used for all future calculations (according to step 102E), the replacement of anomalous second most recent air time (Ta) values serves to filter or smooth out occasional anomalous measurements.

Specifically, in step 102B, the first and third most recent air time (Ta) values are compared. If these values are within a particular percentage of one another (e.g., if the first most recent air time (Ta) value is 5% greater than or less than the third most recent air time (Ta) value), then the routine proceeds to step 102C. If the first and third air time (Ta) values are not within the particular percentage of one another, then the routine proceeds directly to step 102E. That is, if there is too great a difference between the first and third most recent air time (Ta) measurements, then it is assumed that the user has changed speeds between those two measurements, and to reset the second most recent air time (Ta) value in such a situation likely would result in inaccurate air time (Ta) values, rather than the smoothed values obtained when the first and third most recent air time (Ta) measurements are similar.

If step 102C is reached, then the first and second most recent air time (Ta) values are compared. If the first most recent air time (Ta) value is not within a particular percentage of the second most recent air time (Ta) value (e.g., if the first most recent air time (Ta) value is not 5% greater than or less than the second most recent air time (Ta) value), then (in step 102D) the second most recent air time (Ta) value is replaced with an average of the first and third most recent air time (Ta) values, thereby eliminating the apparently anomalous second most recent air time (Ta) measurement.

Finally, according to step 102E, the third most recent air time (Ta) value is used for all future calculations involving air time (Ta) measurements. Thus, because this third most recent air time (Ta) value was a second most recent air time (Ta) value in a previous iteration of loop 101, it would have been "smoothed" during that iteration had it appeared anomalous based upon the comparisons done in steps 102B and 102C above.

High-level step 104 (shown in FIG. 10) includes sub-steps 104A and 104B. As shown in FIG. 12, in step 104A, a cumulative total of air time (Ta) measurements (TaSum) from past iterations of loop 101 is updated with the third most recent air time (Ta) value from step 102E to obtain an updated value of TaSum (i.e., TaSum=TaSum+Ta).

Next, in step 104B, a running total of the number of air time (Ta) steps (TaSteps) is incremented by one (i.e., TaSteps=TaSteps+1). An air time step occurs each time that a positive spike event (identified in step 108B, described below) is followed by a negative spike vent (identified in step 100B).

In step 106 of loop 101, the system is put in a sleep-mode for a particular amount of time before proceeding to step 108A. According to one embodiment, this sleep mode lasts for a time equal to the minimum foot contact time (Tc) that might occur when a user is running at a maximum rate of speed (e.g., 122 milliseconds (ms)). This sleep period is used to prevent the micro-controller from falsely identifying the ringing that occurs in the accelerometer output signal immediately following a detected negative spike event as a subsequent positive spike event. In addition, the power supply to non-critical components in the circuit may be lowered or eliminated during the sleep period to conserve power in the system.

After the sleep period of step 106, loop 101 proceeds to steps 108A–108E, which constitute high-level step 108 (shown in FIG. 10). In steps 108A and 108B, the analog voltages at inputs 46 and 48 of micro-controller 40 are sampled (in step 108A) until a positive spike event is detected (in step 108B) in the voltage at input 46 that is indicative of the foot of a user leaving the ground. According to one embodiment, the analog voltages at inputs 46 and 48 are sampled until the voltage at input 46 rises to greater than 10 levels (of a possible 256 discrete voltage levels) above the level of reference input 48, which should remain approximately at level 128 (i.e., at approximately 2.5 volts on a 5-volt scale). 10 levels corresponds to approximately 0.20 volts on a 5-volt scale. This sampling is done at a rate of 500 samples per second.

Once a positive spike event is detected in step 108B, the foot contact time (Tc) timer is stopped (in step 108C) and the foot air time (Ta) timer is started (in step 108D). The contact time (Tc) timer would have been started (in step 100D) responsive to the detection of a negative spike event (in step 100B) during a previous loop of continuous-loop routine 101. Thus, the contact time (Tc) timer, when stopped in step 108C, provides a measurement of the foot contact time of a user during a footstep of the user, i.e., the time period during which the foot of the user is in physical contact with the ground during a footstep.

In step 108E, the time measured by the contact time (Tc) timer is evaluated to determine whether it falls within an acceptable range of foot contact times. If the measured contact time (Tc) value is not within this acceptable range, then the routine returns to step 100A for the identification of another negative spike event. According to one embodiment, an acceptable range of foot contact times is between 140 and 900 ms.

After evaluating the measured contact time (Tc) value (in step 108E), continuous-loop 101 proceeds to steps 110A–110F, which are included in "FIFO smoothing" step 110 of the high-level routine shown in FIG. 10. During steps 110A–110E, the three most recent foot contact time values, i.e., the three most recent contact time (Tc) values, which have been stored in memory, are analyzed as follows.

First, during step 110A, the three most recent contact time (Tc) values (from prior iterations of loop 101) are shifted to account for the newly-acquired contact time (Tc) value (in step 108C). Specifically, the existing third most recent contact time (Tc) value is discarded, the existing second most recent contact time (Tc) value becomes the new third most recent value, the existing first most recent value becomes the new second most recent contact time (Tc) value, and the newly-acquired contact time (Tc) value becomes the new first most recent contact time (Tc) value.

Next, in steps 110B and 110C, the three most recent contact time (Tc) values (after being shifted in step 110A) are compared, as described below, to ascertain whether the middle contact time (Tc) value (i.e., the second most recent contact time (Tc) value) appears to be anomalous. An anomalous contact time (Tc) measurement (i.e., an anomalous contact time (Tc) value) might occur, for example, when a user steps on a rock or slips on water or ice during a footstep. If the second most recent contact time (Tc) value appears to be the result of an erroneous measurement, then (in step 110D) it is replaced with an average of the first and third most recent contact time (Tc) values. Thus, because only the third most recent contact time (Tc) value is used for all future calculations (according to step 110E), the replacement of anomalous second most recent contact time (Tc) values serves to filter or smooth out occasional anomalous measurements.

Specifically, in step 110B, the first and third most recent contact time (Tc) values are compared. If these values are within a particular percentage of one another (e.g., if the first most recent contact time (Tc) value is 5% greater than or less than the third most recent contact time (Tc) value), then the routine proceeds to step 110C. If the first and third most recent contact time (Tc) values are not within the particular percentage of one another, then the routine proceeds directly to step 110E. That is, if there is too great a difference between the first and third most recent contact time (Tc) measurements, then it is assumed that the user has changed pace between those two measurements, and to reset the second most recent contact time (Tc) value in such a situation likely would result in an inaccuracy, rather than the smoothed values obtained when the first and third most recent contact time (Tc) measurements are similar.

If step 110C is reached, then the first and second most recent contact time (Tc) values are compared. If the first most recent contact time (Tc) value is not within a particular percentage of the second most recent contact time (Tc) value (e.g., if the first most recent contact time (Tc) value is not 5% greater than or less than the second most recent contact time (Tc) value), then (in step 110D) the second most recent contact time (TC) value is replaced with an average of the first and third most recent contact time (Tc) values, thereby eliminating the apparently anomalous second most recent contact time (Tc) measurement.

Finally, according to step 110F, the third most recent contact time (Tc) value is used for all future calculations involving foot contact time (Tc) measurements. Thus, because this third most recent contact time (Tc) value was a second most recent contact time (Tc) value in a previous iteration of loop 101, it would have been "smoothed" during that iteration had it appeared anomalous based upon the comparisons done in steps 110B and 110C above.

Although not shown in FIG. 12, the measured foot contact time also could be used to determine a moment that the user's foot is in its "zero position" during each stride taken by the user, i.e., a moment that the bottom surface of the user's foot is parallel to the surface on which the user is walking, jogging or running. This moment could be determined, for example, by assuming that the user's foot is in its zero position mid-way (or a particular percentage-way) through the measured foot contact time for each stride.

High-level step 112 (shown in FIG. 10) includes sub-steps 112A and 112B. As shown in FIG. 12, in step 112A, a cumulative total of contact time (Tc) measurements (TcSum) from past iterations of loop 101 is updated with the third most recent contact time (Tc) measurement from step 110E to obtain an updated value of the variable TcSum (i.e., TcSum=TcSum+Tc).

Next, in step 112B, a running total of the number of foot contact time (Tc) steps (TcSteps) is incremented by one (i.e., TcSteps=TcSteps+1). An foot contact time step (TcStep) occurs each time that a negative spike event (identified in step 100B) is followed by a positive spike event (identified in step 108B), described above.

In step 114 of loop 101, the system is put in a sleep-mode for a particular amount of time before returning to step 100A. According to one embodiment, this sleep mode lasts for a time equal to the minimum foot contact time (Tc) that might occur when a user is running at a maximum rate of speed (e.g., 122 ms). This sleep period is used to prevent the micro-controller from falsely identifying the ringing that occurs in the accelerometer output signal immediately following a detected positive spike event as a subsequent negative spike event. In addition, the power supply to non-critical components in the circuit may be lowered or eliminated during the sleep period to conserve power in the system.

Figure 13:
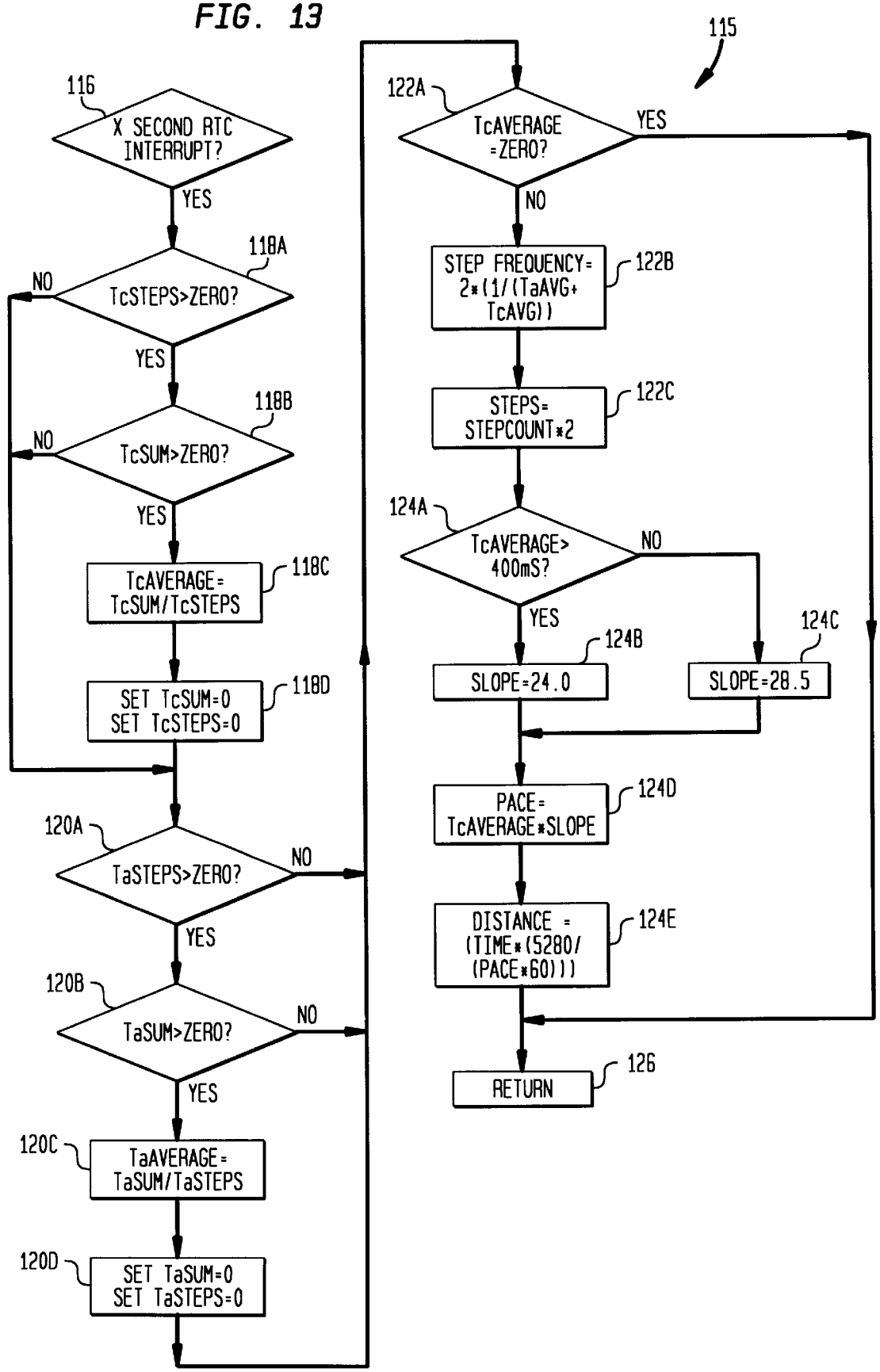
FIG. 13 is a more detailed flow diagram of the interrupt portion of the method shown in FIG. 11.

FIG. 13 shows a lower-level flow chart of interrupt routine 115. As mentioned previously, interrupt routine 115 periodically interrupts continuous-loop 101 so that it may evaluate and analyze the data accumulated by multiple iterations of the loop, e.g., foot contact times and foot loft times. Interrupt routine 115 may programmed to run at any given time interval, but preferredly should not be run any more frequently than once every two seconds so that meaningful data may be gathered by loop 101 before such data is analyzed and evaluated by routine 115.

Step 116 of interrupt routine 115 causes the routine to interrupt continuous-loop 101. Next, steps 118A–118D, which constitute high-level step 118 in FIG. 11, calculate the average contact time (Tc) value (TcAverage) over several steps of a user and reset the TcSum and TcSteps values in loop 101 to zero. Specifically, steps 118A and 118B, respectively, evaluate the current values of TcSteps and TcSum to make sure that each of them is greater than zero. This is done to prevent the micro-controller from performing any divisions by a value of zero. Next, in step 118C, an average foot contact time value (TcAverage) is calculated by dividing the value of TcSum by the value of TcSteps (i.e., TcAverage=TcSum/TcSteps, wherein "/" is the division operator). Finally, the values of TcSum and TcSteps are reset to zero (in step 118D) so that fresh measurements of foot contact times may be made upon return to continuous-loop 101.

Similarly, steps 120A–120D), which constitute high-level step 120 in FIG. 11, calculate the average air time (Ta) value (TaAverage) over several steps of a user and reset the TaSum and TaSteps values in loop 101 to zero. Specifically, steps 120A and 120B, respectively, evaluate the current values of TaSteps and TaSum to make sure that each of them is greater than zero. Next, in step 120C, an average foot air time value (TaAverage) is calculated by dividing the value of TaSum by the value of TaSteps (i.e., TaAverage=TaSum/TaSteps). Finally, the values of TaSum and TaSteps are reset to zero (in step 120D) so that fresh measurements of foot air times may be made upon return to continuous-loop 101.

In steps 122A–122C, which constitute high-level step 122 in FIG. 11, the step frequency of the user is determined based on the calculated TcAverage and TaAverage values, and the total number of steps of the user is calculated by multiplying the StepCount value from loop 101 by two. Specifically, step 122A evaluates the current value of TcAverage to make sure that it is greater than zero. This is done to prevent the micro-controller from performing any divisions by a value of zero. Next, in step 122B, the step frequency of the user is calculated by taking the inverse of two times the average air time value (TaAverage) plus the average foot contact time value (TcAverage)(i.e., Step Frequency=2*(1/TaAverage+TcAverage)), wherein "*" is the multiplication operator).

Next, in steps 124A–124E, the pace of the user (Pace) is calculated according to a known algorithm (described below), and the distance traveled by the user is calculated by multiplying the time period in which the pace was determined by the rate at which the user is moving. The rate of the user (in feet-per-second) is equal to the quantity (5280/ (Pace*60)). This distance measurement could be cumulative of past distance measurements to determine a total distance traveled. The cumulative distance value, therefore, would be resettable by a user so the user could measure distance traveled from a zero reference point.

Specifically, in step 124A, the average foot contact time value (TcAverage), which was calculated in step 118, is evaluated to determine whether it is greater than or less than 400 ms. If TcAverage is less than 400 ms, then a variable "Slope" is set (in step 124B) to a value of 24, and if TcAverage is greater than 400 ms, then the variable Slope is set (in step 124C) to a value of 28.5. Next, in step 124D, the pace of the user (Pace) is calculated by multiplying the value TcAverage by the variable Slope (i.e., Pace= TcAverage*Slope).

The present inventors have discovered that it is advantageous to use at least two distinct equations to derive the pace of the user based upon the measured foot contact time. That is, for a measured foot contact time that is less than a particular value (e.g., 400 ms), a first equation should be used to derive the pace of the user therefrom, while for a measured foot contact time that is greater than the particular value (e.g., 400 ms), a second equation should be used.

Figure 14:
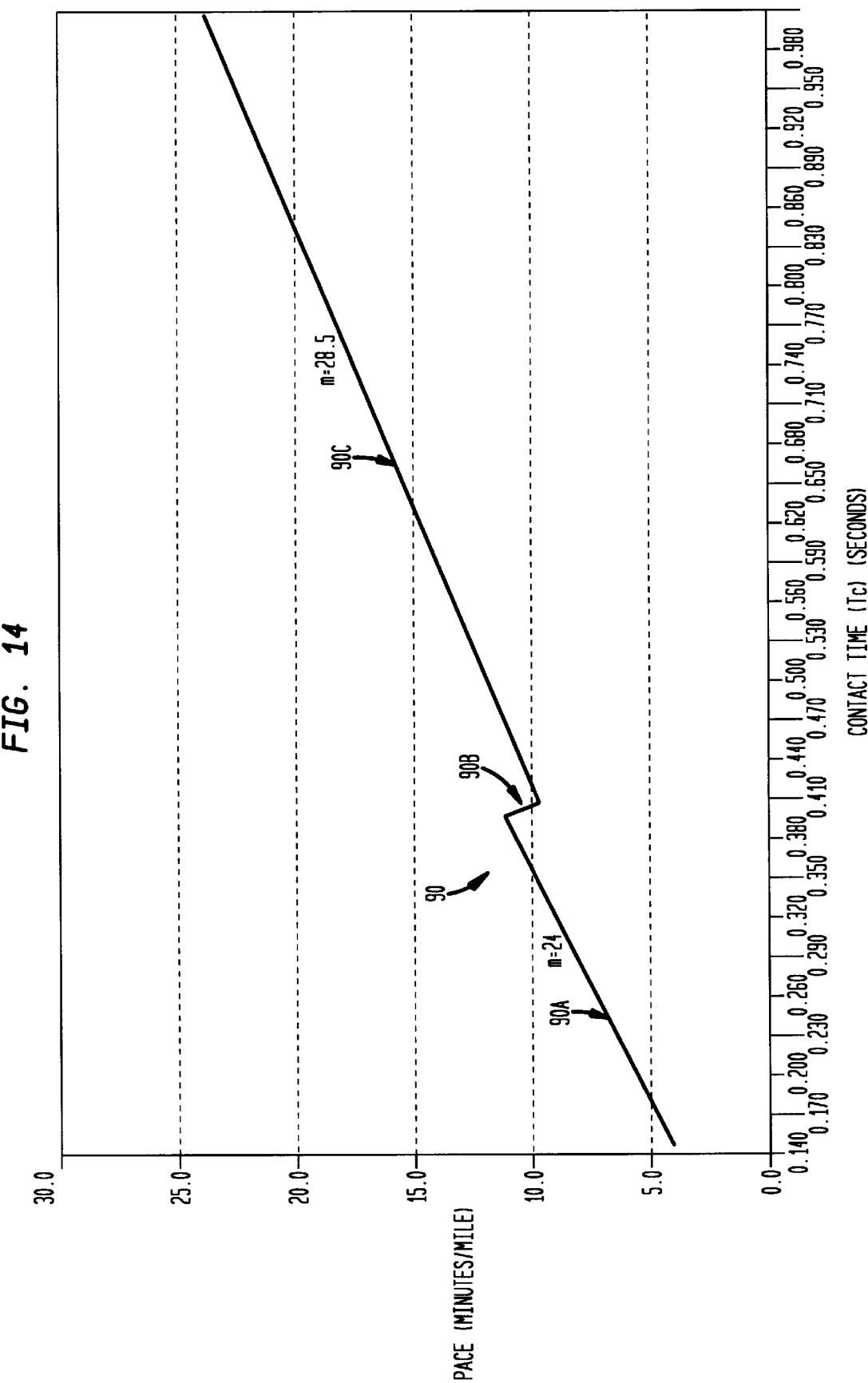
FIG. 14 is a graph illustrating how the pace of a user in locomotion may be determined based upon the average measured foot contact time of a foot of the user.

Referring to FIG. 14, a graph showing the discovered relationship between foot contact time (Tc) and the pace of a user (Pace) is provided. As shown, curve 90 has distinct segments 90A, 90B and 90C. Each of line segments 90A and 90C has a different slope, but both share a common y-intercept value at zero minutes-per-mile. It has been discovered that the average foot contact time of a user does not tend to fall within the range covered by line segment 90B, regardless of whether the user is walking, jogging or running. Therefore, one of line segments 90A or 90C may always be used to determine a pace of the user based upon the measured foot contact time. As shown in FIG. 14, the slope of line segment 90A is 24. This slope is used as the variable Slope (in Step 124B of FIG. 13) when the average measured foot contact time falls under line segment 90A, i.e., when TcAverage is less than 400 ms. Similarly, the slope of line segment 90C is 28.5, and this slope is used as the variable Slope (in step 124C of FIG. 13) when the average measured foot contact time falls under line segment 90C, i.e., when TcAverage is greater than 400 ms.

Referring again to FIG. 13, in step 124E, the distance traveled by a user in locomotion (Distance), as mentioned above, is calculated using the following equation: Distance= (time*(5280/(Pace*60))), wherein "time" is the interrupt period of interrupt routine 115 (e.g., two or more seconds).

Finally, after the calculations in steps 124A–E, and/or any other desired calculations, are performed, step 126 returns interrupt routine 115 to continuous-loop 101 for further measurements of contact time (Tc) and air time (Ta) values.

In addition to calculating a user's pace, rate of travel, and distance traveled, metabolic energy expenditure may also be calculated based upon the measured foot contact time of a user. One approach to measuring metabolic energy expenditure based upon foot contact time is described by two of the inventors of the present invention in co-pending U.S. patent application Ser. No. 08/255,820, filed on Apr. 11, 1994, which is incorporated herein by reference.

Referring briefly back to FIGS. 1 and 3, according to one embodiment, several variables or parameters could be input by the user for use by the software routine described above. These variables or parameters could be input, for example, via user interface 32 in FIG. 1 or user interface 58 in FIG. 3. Although the present invention is intended to be completely self-adjusting and ideally should not require the input of any user-specific data, it is envisioned that certain parameters and variables may be user-adjustable to accommodate individual users. For example: (1) the threshold values for the positive and negative spike events (identified in steps 108B and 100B, respectively of FIG. 12) could be adjusted, (2) the sleep times of steps 106 and 114 of FIG. 12 could be adjusted, (3) the slopes of the various portions of line segment 90 (in FIG. 14) could be adjusted or additional line segments could be added or alternative contact time/pace equations could be employed in their stead, or (4) the acceptable range of foot contact time (Tc) values determined in step 108E of FIG. 12 could be altered.

Such parameters or variables could have default values pre-programmed into the system, which default values could then be adjusted by the user according to certain user-specific criteria such as height, weight, or shoe hardness.

Alternatively, the parameters or variables could be adjusted automatically via software, based upon information input by the user (such as the pushing of a button both when the user starts and when the user finishes traversing a known distance).

It should be understood that while the invention has been described herein as using a particular accelerometer and a particular micro-controller to perform its various functions, any devices performing similar functions, including hard-wired circuitry, could equivalently be employed without departing from the intended scope of the invention. Additionally, while a specific embodiment of a high-pass filter/amplifier circuit is described herein, the scope of the invention is not intended to be limited by the particular characteristics of this embodiment. Further, while a highly-specific software routine has been described herein, the particular characteristics of this routine should also not be regarded as limiting the scope of the invention.

Having thus described at least one illustrative embodiment of the invention, various alterations, modifications and improvements will readily occur to those skilled in the art. Such alterations, modifications and improvements are intended to be within the spirit and scope of the invention. Accordingly, the foregoing description is by way of example only and is not intended as limiting. The invention is limited only as defined in the following claims and the equivalents thereto.

What is claimed is:

1. A method for analyzing activity of a person in locomotion on foot on a surface, comprising steps of:
   (a) using a sensor to generate a signal in response to movement of the person when the person is in locomotion without exerting compression forces on the sensor to generate the signal; and
   (b) analyzing the signal to determine a moment that the foot leaves the surface during a footstep taken by the person.

2. The method of claim 1, further comprising a step of:
   (c) analyzing the signal to determine a moment that the foot comes into contact with the surface during the footstep taken by the person.

3. The method of claim 2, further comprising a step of:
   (d) determining a foot contact time based upon a time difference between the moment the foot comes into contact with the surface determined in the step (c) and the moment the foot leaves the surface determined in the step (b).

4. The method of claim 3, further comprising a step of:
   (e) using the foot contact time determined in the step (d) to determine a rate at which the person is moving relative to the surface.

5. The method of claim 3, further comprising a step of:
   (e) using the foot contact time determined in the step (d) to determine a distance traveled by the person while in locomotion.

6. The method of claim 3, further comprising a step of:
   (e) using the foot contact time determined in the step (d) to determine an amount of energy expended by the person while in locomotion.

7. The method of claim 3, further comprising steps of:
   (e) repeating the steps (a) (b), (c) and (d) to determine a plurality of foot contact times;
   (f) averaging the plurality of foot contact times determined in the step (e) to determine an average foot contact time; and
   (g) using the average foot contact time determined in the step (f) to determine at least one of a rate at which the person is moving relative to the surface, a distance traveled by the person while in locomotion, and an amount of energy expended by the person while in locomotion.

8. The method of claim 2, further comprising a step of:
   (d) determining a foot loft time based upon a time difference between the moment the foot leaves the surface determined in the step (b) and the moment the foot comes into contact with the surface determined in the step (c).

9. A device for analyzing activity of a person in locomotion on foot on a surface, comprising:
   a sensor to be supported in relation to the foot, the sensor being configured and arranged to provide an output signal in response to movement of the foot during at least one footstep taken by the person without requiring compression forces thereon to generate the signal; and
   a signal processor coupled to the sensor to receive the output signal therefrom, the signal processor being configured to analyze the output signal of the sensor to determine at least one moment that the foot leaves the surface during the at least one footstep.

10. The device of claim 9, wherein the signal processor is configured to analyze the output signal of the sensor to determine at least one moment that the foot comes into contact with the surface.

11. The device of claim 10, wherein the signal processor is configured to analyze the output signal of the sensor to determine at least one time period that the foot was in contact with the surface during at least one stride taken by the foot based upon a time difference between the at least one moment that the foot came into contact with the surface and the at least one moment that the foot left the surface.

12. The device of claim 11, wherein the signal processor is configured to use the at least one time period that the foot was in contact with the surface to determine at least one of a rate at which the person is moving relative to the surface, a distance traveled by the person while in locomotion, and an amount of energy expended by the person while in locomotion.

13. The device of claim 10, wherein the signal processor is configured to analyze the output signal of the sensor to determine at least one time period that the foot was not in contact with the surface between strides taken by the foot based upon a time difference between the at least one moment that the foot left the surface and the at least one moment that the foot came into contact with the surface.

14. A method for monitoring activity of a person in locomotion on foot, comprising steps of:
   (a) using a first electronic device to determine at least one foot contact time of the person; and
   (b) transmitting information, via a wireless communication channel, from the first electronic device to a second electronic device, which information is based upon the at least one foot contact time determined in the step (a).

15. The method of claim 14, further comprising a step of:
   (c) using the second electronic device to display a variable which is based upon the information transmitted in the step (b).

16. The method of claim 14, further comprising a step of:
   (c) using the second electronic device to display a distance traveled by the person which is based on the information transmitted in the step (b).

17. The method of claim 14, further comprising a step of:
(c) using the second electronic device to display a pace of the person which is based on the information transmitted in the step (b).

18. A system for monitoring activity of a person in locomotion on foot, comprising:
a first electronic device to measure at least one foot contact time of the person; and
a second electronic device, coupled to the first electronic device via a wireless communication channel, to receive information from the first electronic device which is based upon the at least one foot contact time measured by the first electronic device.

19. The system of claim 18, wherein the second electronic device includes a display to display a variable which is based upon the information received from the first electronic device over the wireless communication channel.

20. The system of claim 18, wherein the second electronic device includes a display to display a distance traveled by the person which is based upon the information received from the first electronic device over the wireless communication channel.

21. A method for analyzing activity of a person in locomotion on foot on a surface, comprising steps of:
(a) mounting a sensor above a bottom surface of the foot so that the sensor generates a signal in response to movement of the person when the person is in locomotion; and
(b) analyzing the signal to determine a moment that a foot of the person leaves the surface during a footstep taken by the person.

22. The method of claim 21, further comprising a step of:
(c) analyzing the signal to determine a moment that the foot comes into contact with the surface during the footstep taken by the person.

23. The method of claim 22, further comprising a step of:
(d) determining a foot contact time based upon a time difference between the moment that the foot comes into contact with the surface determined in the step (c) and the moment that the foot leaves the surface determined in the step (b).

24. The method of claim 23, further comprising a step of:
(e) using the foot contact time determined in the step (d) to determine a rate at which the person is moving relative to the surface.

25. The method of claim 23, further comprising a step of:
(e) using the foot contact time determined in the step (d) to determine a distance traveled by the person while in locomotion.

26. The method of claim 23, further comprising a step of:
(e) using the foot contact time determined in the step (d) to determine an amount of energy expended by the person while in locomotion.

27. The method of claim 23, further comprising steps of:
(e) repeating the steps (a), (b), (c) and (d) to determine a plurality of foot contact times;
(f) averaging the plurality of foot contact times determined in the step (e) to determine an average foot contact time; and
(g) using the average foot contact time determined in the step (f) to determine at least one of a rate at which the person is moving relative to the surface, a distance traveled by the person while in locomotion, and an amount of energy expended by the person while in locomotion.

28. The method of claim 22, further comprising a step of:
(d) determining a foot loft time based upon a time difference between the moment that the foot leaves the surface determined in the step (b) and the moment that the foot comes into contact with the surface determined in the step (c).

29. A device for analyzing activity of a person in locomotion on foot on a surface, comprising:
a sensor supported by the person above a bottom surface of a foot of the person, the sensor being configured and arranged to provide an output signal in response to movement of the foot during at least one footstep taken by the person; and
a signal processor coupled to the sensor to receive the output signal therefrom, the signal processor being configured to analyze the output signal of the sensor to determine at least one moment that a foot of the person leaves the surface during the at least one footstep.

30. The device of claim 29, wherein the signal processor is configured to analyze the output signal of the sensor to determine at least one moment that the foot makes contact with the surface.

31. The device of claim 30, wherein the signal processor is configured to analyze the output signal of the sensor to determine at least one time period that the foot was in contact with the surface during at least one stride taken by the foot based upon a time difference between the at least one moment that the foot came into contact with the surface and the at least one moment that the foot left the surface.

32. The device of claim 31, wherein the signal processor is configured to use the at least one time period that the foot was in contact with the surface to determine at least one of a rate at which the person is moving relative to the surface, a distance traveled by the person while in locomotion, and an amount of energy expended by the person while in locomotion.

33. The device of claim 30, wherein the signal processor is configured to analyze the output signal of the sensor to determine at least one time period that the foot was not in contact with the surface between strides taken by the foot based upon a time difference between the at least one moment that the foot left the surface and the at least one moment that the foot came into contact with the surface.

34. A method for analyzing activity of a person in locomotion on foot on a surface, comprising steps of:
(a) using a sensor to generate a signal in response to movement of the person when the person is in locomotion without exerting compression forces on the sensor to generate the signal; and
(b) analyzing the signal to determine at least one of at least one foot contact time and at least one foot loft time of the person during at least one footstep taken by the person.

35. The method of claim 34, wherein the step (a) includes a step of:
(a1) using the sensor to generate the signal such that the signal is indicative of acceleration of a foot of the person.

36. The method of claim 34, wherein the step (b) includes a step of:
(b1) analyzing the signal to determine the at least one foot contact time of the person during the at least one footstep taken by the person.

37. The method of claim 36, further comprising a step of:
(c) using the at least one foot contact time determined in the step (b) to determine a rate at which the person is moving relative to the surface.

38. The method of claim 36, further comprising a step of:
(c) using the at least one foot contact time determined in the step (b) to determine a distance traveled by the person while in locomotion.

39. The method of claim 36, further comprising a step of:
(c) using the at least one foot contact time determined in the step (b) to determine an amount of energy expended by the person while in locomotion.

40. The method of claim 36, further comprising steps of:
(c) repeating the steps (a) and (b) to determine a plurality of foot contact times;
(d) averaging the plurality of foot contact times determined in the step (c) to determine an average foot contact time; and
(e) using the average foot contact time determined in the step (d) to determine at least one of a rate at which the person is moving relative to the surface, a distance traveled by the person while in locomotion, and an amount of energy expended by the person while in locomotion.

41. A device for analyzing activity of a person in locomotion on foot on a surface, comprising:
(a) a sensor to be supported in relation to a foot of the person, the sensor being configured and arranged to provide a signal in response to movement of the foot during at least one footstep taken by the person without requiring compression forces thereon to generate the signal; and
(b) a signal processor coupled to the sensor to receive the signal therefrom, the signal processor being configured to determine at least one of at least one foot contact time and at least one foot loft time of the person during at least one footstep taken by the person.

42. The device of claim 41, wherein the sensor includes an accelerometer.

43. The device of claim 41, wherein the signal processor is configured to analyze the signal to determine the at least one foot contact time of the person during the at least one footstep taken by the person.

44. The device of claim 43, wherein the signal processor is configured to use the at least one foot contact time to determine a rate at which the person is moving relative to the surface.

45. The device of claim 43, wherein the signal processor is configured to use the at least one foot contact time to determine a distance traveled by the person while in locomotion.

46. The device of claim 43, wherein the signal processor is configured to use the at least one foot contact time to determine an amount of energy expended by the person while in locomotion.

47. A method for analyzing activity of a person in locomotion on foot on a surface, comprising steps of:
(a) mounting a sensor above a bottom surface of a foot of the person so that the sensor generates a signal in response to movement of the person when the person is in locomotion; and
(b) analyzing the signal to determine at least one of at least one foot contact time and at least one foot loft time of the person during at least one footstep taken by the person.

48. The method of claim 47, wherein the step (a) includes a step of:

(a1) using the sensor to generate the signal such that the signal is indicative of acceleration of the foot.

49. The method of claim 47, wherein the step (b) includes a step of:
(b1) analyzing the signal to determine the at least one foot contact time of the person during the at least one footstep taken by the person.

50. The method of claim 49, further comprising a step of:
(c) using the at least one foot contact time determined in the step (b) to determine a rate at which the person is moving relative to the surface.

51. The method of claim 49, further comprising a step of:
(c) using the at least one foot contact time determined in the step (b) to determine a distance traveled by the person while in locomotion.

52. The method of claim 49, further comprising a step of:
(c) using the at least one foot contact time determined in the step (b) to determine an amount of energy expended by the person while in locomotion.

53. The method of claim 49, further comprising steps of:
(c) repeating the step (b) to determine a plurality of foot contact times for a plurality of footsteps taken by the person;
(d) averaging the plurality of foot contact times determined in the step (c) to determine an average foot contact time; and
(e) using the average foot contact time determined in the step (d) to determine at least one of a rate at which the person is moving relative to the surface, a distance traveled by the person while in locomotion, and an amount of energy expended by the person while in locomotion.

54. A device for analyzing activity of a person in locomotion on foot on a surface, comprising:
(a) a sensor to be supported by the person above a bottom surface of a foot of the person, the sensor being configured to generate a signal in response to movement of the person when the person is in locomotion; and
(b) a signal processor coupled to the sensor to receive the signal therefrom, the signal processor being configured to determine at least one of at least one foot contact time and at least one foot loft time of the person during at least one footstep taken by the person.

55. The device of claim 54, wherein the sensor includes an accelerometer.

56. The device of claim 54, wherein the signal processor is configured to analyze the signal to determine the at least one foot contact time of the person during the at least one footstep taken by the person.

57. The device of claim 56, wherein the signal processor is configured to use the at least one foot contact time to determine a rate at which the person is moving relative to the surface.

58. The device of claim 56, wherein the signal processor is configured to use the at least one foot contact time to determine a distance traveled by the person while in locomotion.

59. The device of claim 56, wherein the signal processor is configured to use the at least one foot contact time to determine an amount of energy expended by the person while in locomotion.

* * * * *